US006673538B1

(12) United States Patent
Goldstein

(10) Patent No.: US 6,673,538 B1
(45) Date of Patent: Jan. 6, 2004

(54) METHODS AND COMPOSITIONS FOR DESIGNING VACCINES

(75) Inventor: Richard N. Goldstein, Cambridge, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/463,587

(22) PCT Filed: Jul. 24, 1998

(86) PCT No.: PCT/US98/15462
§ 371 (c)(1),
(2), (4) Date: Apr. 21, 2000

(87) PCT Pub. No.: WO99/04637
PCT Pub. Date: Feb. 4, 1999

Related U.S. Application Data

(60) Provisional application No. 60/053,097, filed on Jul. 25, 1997.

(51) Int. Cl.[7] ............................. C12Q 1/68; C12N 7/00
(52) U.S. Cl. ........................................ 435/6; 435/243
(58) Field of Search ....................... 435/6, 243

(56) References Cited

U.S. PATENT DOCUMENTS

| | | | |
|---|---|---|---|
| 4,671,958 A | 6/1987 | Rodwell et al. | 424/85 |
| 4,831,122 A | 5/1989 | Buchsbaum et al. | 530/389 |
| 4,867,973 A | 9/1989 | Goers et al. | 424/85.91 |
| 4,957,738 A | 9/1990 | Patarroyo | 424/88 |
| 4,958,009 A | 9/1990 | Bjorn et al. | 530/389 |
| 4,980,457 A | 12/1990 | Jansen et al. | 530/391 |
| 5,208,021 A | 5/1993 | Johnson et al. | 424/85.91 |
| 5,332,567 A | 7/1994 | Goldenberg | 424/1.49 |
| 5,364,762 A | 11/1994 | Dornmair et al. | 435/7.24 |
| 5,487,982 A | 1/1996 | Salter | 435/69.1 |
| 5,495,423 A | 2/1996 | DeLisi et al. | 364/496 |
| 5,518,888 A | 5/1996 | Waldman | 435/7.23 |
| 5,578,706 A | 11/1996 | Ghetie et al. | 530/391.7 |
| 5,608,039 A | 3/1997 | Pastan et al. | 530/387.3 |
| 5,635,603 A | 6/1997 | Hansen et al. | 530/391.5 |
| 5,641,491 A | 6/1997 | Wilson et al. | |
| 5,652,342 A | 7/1997 | Zimmerman et al. | 530/403 |
| 5,657,255 A | 8/1997 | Fink et al. | 364/578 |

OTHER PUBLICATIONS

Zingg, B. C. et al., "Comparative Analysis of Genetic Variability among Borrelia burgdorferi Isolates from Europe and the United States by Restriction Enzyme Analysis, Gene Restriction Fragment Length Polymorphism . . . ", J. Clin. Microbiol., vol. 31, pp. 3115–3122 (1993).*

Gravelle et al., "The Targeting of CD4+ T Lymphocytes to A B Cell Lymphoma. A Comparison of Anti–CD3–Anti–Idiotype Antibody Conjugates and Antigen–Anti–Idiotype Antibody Conjugates", J. Immunology, 142 4079–4084 (1989).

Ihle et al., "Antibody–targeted Superantigens Induce Lysis of Major Histocompatibility Complex Class II–negative T–cell Leukemia Lines," Cancer Research, 55, 623–628 (1995).

Reiter et al., "Peptide–specific killing of antigen–presenting cells by a recombinant antibody–toxin fusion protein targeted to major histocompatibility complex/peptide class I complexes with T cell receptor–like specificity", Proc. Natl. Acad. Sci. USA 94, 4631–4636 (1997).

(List continued on next page.)

Primary Examiner—BJ Forman
Assistant Examiner—Teresa Strzelecka
(74) Attorney, Agent, or Firm—Weingarten, Schurgin, Gagnebin & Lebovici LLP

(57) ABSTRACT

Methods and compositions are described for determining a statistically significant number of different strains within a species of bacteria indicative of the species population structure as a whole in order to permit the evaluation of a vaccine target.

14 Claims, 20 Drawing Sheets

OTHER PUBLICATIONS

Holzer et al., "T–cell stimulation and cytokine release induced by staphylococcal enterotoxin A (SEA) and the SEAD227A mutant", Immunology, 90 74–80 (1997).

Carayanniotis et al., "Adjuvant–free IgG responses induced with antigen coupled to antibodies against class II MHC", Nature, 327 59–61 (1987).

Snider et al., "Targeted Antigen Presentation Using Crosslinked Antibody Hetroaggregates", J. Immunology, 139 1609–1616 (1987).

Berg et al., "Comparing macrophages and dendritic leukocytes as antigen–presenting cells for humoral responses in vivo by antigen targeting", Eur. J. Immunol., 24 1262–1268 (1994).

Snider et al., "Intranasal antigen targeting to MHC class II molecules primes local IgA and serum IgG antibody response in mice", 90 323–329 (1997).

Juliano, "Drug Delivery Systems. Characteristics and Biomedical Applications", Chapter 8, Oxford University Press, New York (1980).

Steinbach et al., "Transmissibility of Pseudomonas Cepacia Infection in Clinin Patients and Lung–Transplant Recipients with Cystic Fibrosis", N.E.J. of Med., 331 981–987 (1994).

Goldstein et al., "Structurally Variant Classes of Pilus Appendage Fibers Coexpressed from Burkholderia (Pseudomonas) cepacia", J. Bacteriology, 177 No. 4, 1039–1052 (1995).

Sun et al., "The Emergence of a Highly Transmissible Lineage of cbl+ Pseudomonas (Burkholderia) cepacia causing CF centre Epidemics in North America and Britain", Nature Medicine, 1 No. 7, 661–666 (1995).

Arthur et al., "Restriction Fragment Length Polymorphisms Among Uropathogenic *Escherichia Coli* Isolates: Pap–Related Sequences Compared with rrn Operons," Infection and Immunity, 58 No. 2, 471–479 (1990).

Karaolis et al., "The Sixth and Seventh Cholera Pandemics are due to Independent Clones Separately Derived from Environmental, Nontoxigenic, non–O1 *Vibrio cholerae*", Journal of Bacteriology, Jun. 1995, vol 117, No. 11, pp. 3191–3198.

Ellis et al., "Variation in Cultural, Morphological, Biochemical Properties and Infectivity of Australian Isolates of Dermatophilus congolensis", Veterinary Microbiology, 1993, vol. 38, pp. 81–102.

Wilske et al., "Antigenic Variation and Strain Hetrogeneity in *Borrelia spp*", Research in Microbiology, 1992, vol. 143, pp. 583–596.

Mahan. S.M., "Review of the Molecular Biology of *Cowdria ruminantium*", Veterinary Parasitology, 1995, vol. 57, pp. 51–56.

O'Hanley et al., "Genetic Conservation of hylA Determinants and Serological Conservation of HlyA: Basis for Developing a Broadly Cross–reactive Subunit *Escherichia coli* alpha–hemolysin vaccine", Infection and Immunity, Mar. 1993, vol. 61, No. 3, pp. 1091–1097.

Barbet, A. F., "Recent Developments in the Molecular Biology of Anaplasmosis", Veterinary Parasitology, 1995, vol. 57, pp. 43–49.

Dykhuizen et al., "Borella burgdorferi is Clonal: Implications for Taxonomy and Vaccine Development", Proc. Natl. Acad. Sci. USA, Nov. 1993, vol. 90, pp. 10163–10167.

* cited by examiner

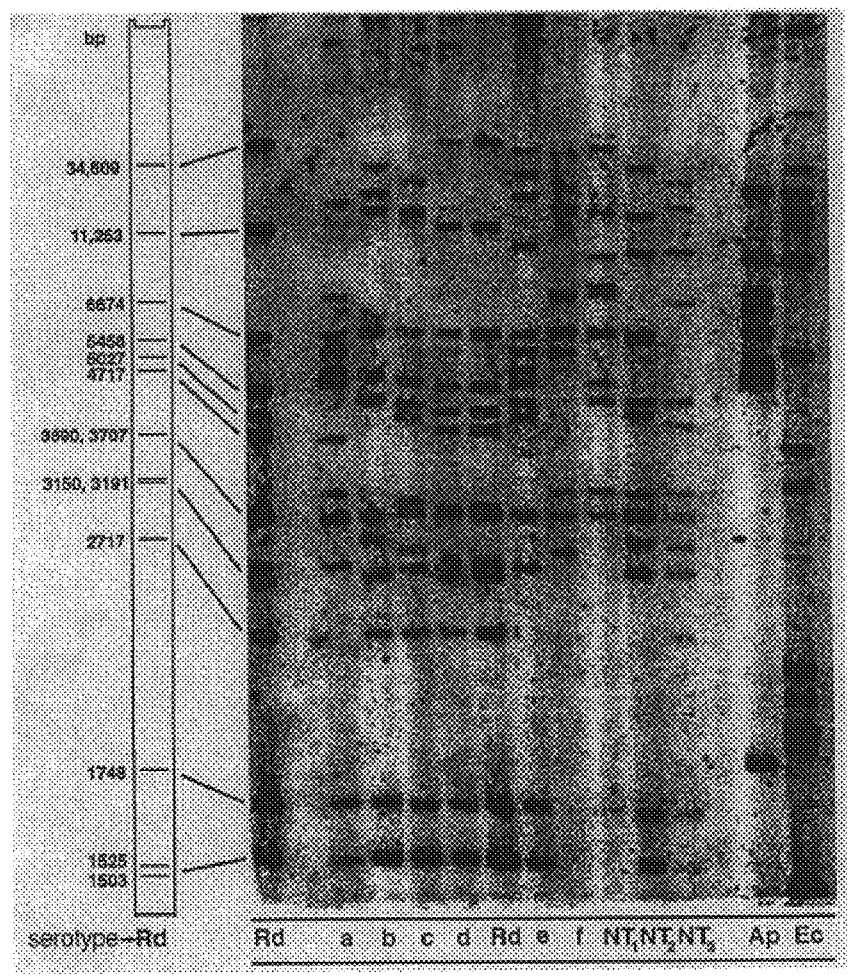

LEGEND.
Leftmost portion of the figure depicts the predictable EcoRI ribotype RFLP profile of the genomically sequenced H. influenzae strain Rd. Actual RFLP profiles of this strain appears in lanes 1 and 6 (so labeled). Other H. influenzae isolates, as indicated, are serotypes a, c, c, d, e, f and NT (non-typable, i.e. unencapsulated). EcoRI RFLPs of 2 non-H. influenzae isolates are shpwn at the farthestmost right lanes, that for A. pleuroneumonia (Ap) and E. coli (Ec).

*FIG. 2*

LEGEND.
Leftmost portion of the figure depicts the predictable EcoRI ribotype RFLP profile of the genomically sequenced E. coli strain MG1655. Actual RFLP profiles of this strain appear in lanes 1, 8 and 17.

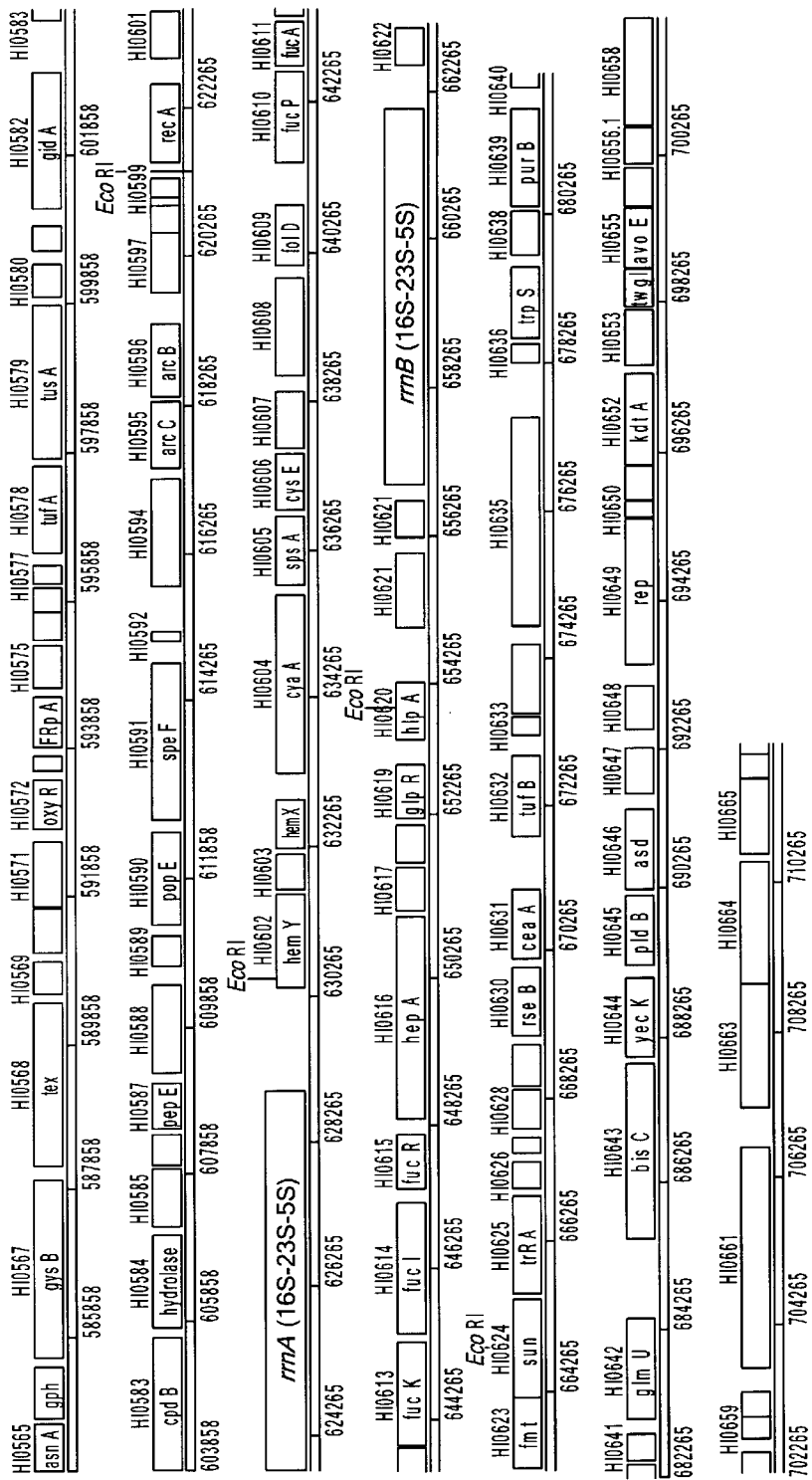

FIG. 5A

LEGEND:
For each of the 6 ribosomal RNA operons, rrnA through rrnF, the 16S-23S-5Sm operon gene cluster is indicated by a black box so labeled. Acronyms of the known flanking genes are written within each of the lightly shaded boxes representative of the known positions of these genes. When such a box in unlabeled, an open reading frame exists of undetermined coding function. All 6 rrn operons, A - F, appear in actual polarity revealed from the genomic sequence of strain Rd.

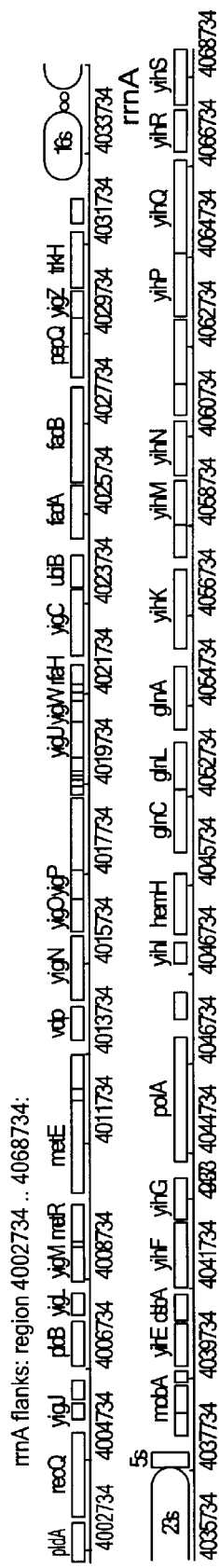

FIG. 6A

LEGEND:
For each of the 7 ribosomal RNA operons, rrnA though rrnH, the 16S-23S-5S genes of the operon are indicated by black cylinders. A small circle(s) between the 16S and 23S genes indicates a transfer RNA gene in this spacer region of the ribosomal RNA operon. Acronyms of the known flanking genes are written above each of the lightly shaded boxes representative of the known positions of these genes. When such a box is unlabeled, an open read frame exists of undetermined coding function. All 7 rrn operons, A - H, appear in actual polarity as revealed from the genomic sequence of strain MG1655.

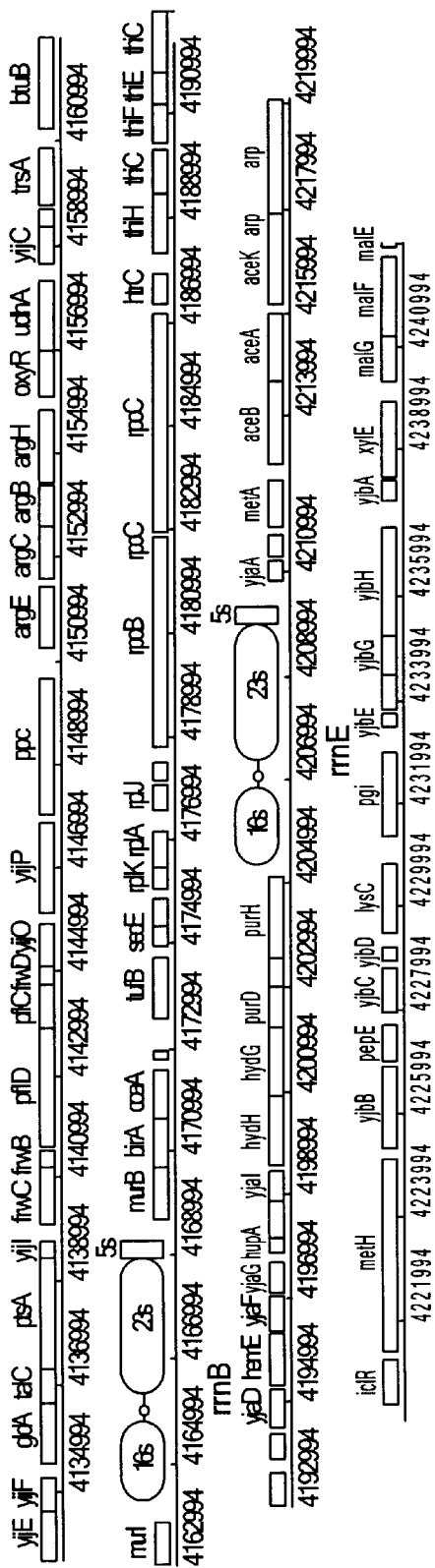

FIG. 6B

LEGEND:
For each of the 7 ribosomal RNA operons, rrnA though rrnH, the 16S-23S-5S genes of the operon are indicated by black cylinders. A small circle(s) between the 16S and 23S genes indicates a transfer RNA gene in this spacer region of the ribosomal RNA operon. Acronyms of the known flanking genes are written above each of the lightly shaded boxes representative of the known positions of these genes. When such a box is unlabeled, an open read frame exists of undetermined coding function. All 7 rrn operons, A - H, appear in actual polarity as revealed from the genomic sequence of strain MG1655.

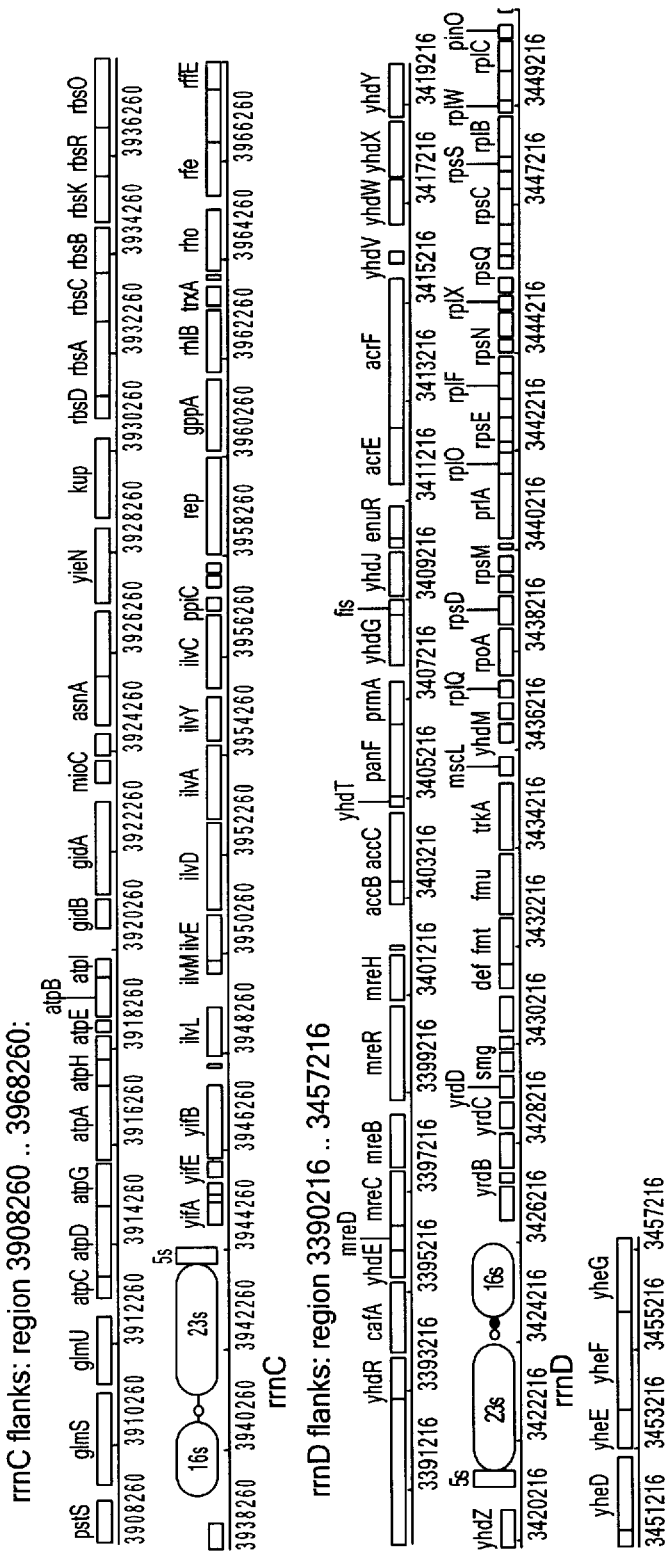

FIG. 6C

LEGEND:
For each of the 7 ribosomal RNA operons, rrnA though rrnH, the 16S-23S-5S genes of the operon are indicated by black cylinders. A small circle(s) between the 16S and 23S genes indicates a transfer RNA gene in this spacer region of the ribosomal RNA operon. Acronyms of the known flanking genes are written above each of the lightly shaded boxes representative of the known positions of these genes. When such a box is unlabeled, an open read frame exists of undetermined coding function. All 7 rrn operons, A - H, appear in actual polarity as revealed from the genomic sequence of strain MG1655.

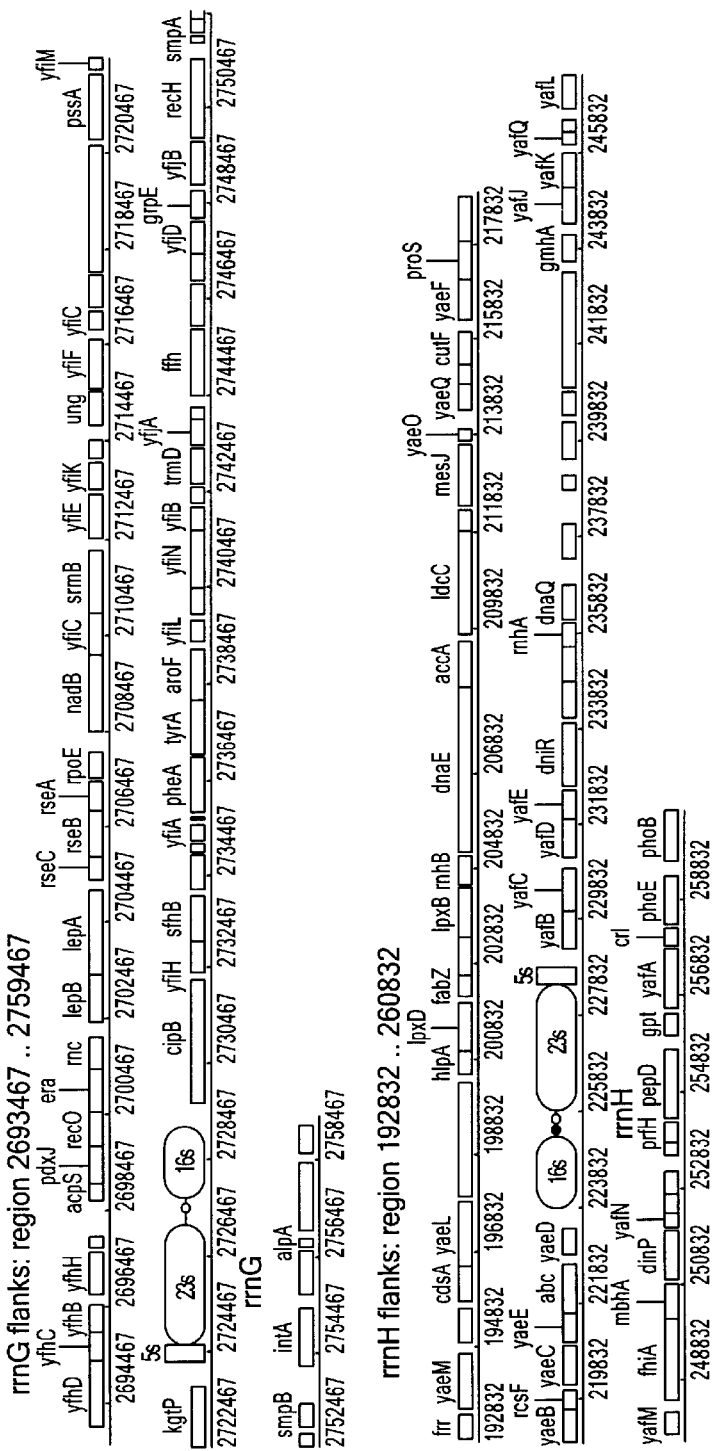

FIG. 6D

LEGEND:
For each of the 7 ribosomal RNA operons, rrnA though rrnH, the 16S-23S-5S genes of the operon are indicated by black cylinders. A small circle(s) between the 16S and 23S genes indicates a transfer RNA gene in this spacer region of the ribosomal RNA operon. Acronyms of the known flanking genes are written above each of the lightly shaded boxes representative of the known positions of these genes. When such a box is unlabeled, an open read frame exists of undetermined coding function. All 7 rrn operons, A - H, appear in actual polarity as revealed from the genomic sequence of strain MG1655.

METHODS AND COMPOSITIONS FOR DESIGNING VACCINES

This application for patent under 35 U.S.C. 111(a) claims priority to Provisional Application Serial No. 60/053,097 filed Jul. 25, 1997 under 35 U.S.C. 111 (b). This invention was made with Government Support under Grant Number DK- RO1-AI37728 awarded by the National Institute of Health. The government may have certain rights in the invention.

FIELD OF THE INVENTION

The present invention relates to the identification of groups within a species, and in particular, methods and compositions for determining a statistically significant number of different strains within a species of bacteria indicative of the species population structure as a whole in order to permit the evaluation of a vaccine target.

BACKGROUND

Bacterial infections continue to account for a considerable amount of human illness. While antibiotic therapy is clearly one of the great success stories of modem medicine, the development of antibiotic resistant strains of important human pathogens has called into question the use of antibiotics as the first line of defense against bacterial pathogens.

Vaccines to a variety of bacteria have been attempted. The best results thus far have involved vaccines directed to specific toxins of the organism (e.g. diphtheria toxoid, tetanus toxoid, etc.). Considerably less favorable results have been achieved with whole organism ("killed bacteria") vaccines (e.g. *Bordetella pertussis, Vibrio cholerae*, etc.). Indeed, immunity induced by vaccination with killed organisms such as *V. cholerae* persists for a only a few months and therefore is of very limited value.

One important problem with current approaches to vaccine development stems from the range of variability within a species of any particular surface antigen considered as a possible vaccine target. This accounts for the fact that only a few important, new bacterial vaccines have been produced in the last 30 years (i.e. for *Haemophilus influenzae* type b, a major cause of meningitis). Moreover, development of even these recent few successful vaccines were a tedious and haphazard endeavor with little progess seen for many years.

What is needed is a more efficient approach to vaccine development. Importantly, the new approach should be one that takes into account the variability in surface antigens within a species.

SUMMARY OF THE INVENTION

The present invention relates to the identification of groups within a species, and in particular, methods and compositions for determining a statistically significant number of different strains within a species of bacteria indicative of the species population structure as a whole in order to permit the evaluation of a vaccine target. The present invention employs a method comprising the grouping of strains within a species to approximate the minimum variability in any vaccine target. This permits the evaluation of the vaccine target in a more limited number of bacterial isolates (as opposed to the two extremes of 1) using but a single isolate and 2) testing hundreds of isolates at random).

In one embodiment of the method of the present invention, the present invention contemplates analysis of the flanking sequences of one or more so-called Ribosomal RNA Operons, each comprising three genes arranged in the order 16S-23S-5S, with "spacer" DNA separating each gene (hereinafter represented by: 5'-16S-spacer-23S-spacer-5S-3'). The present invention contemplates that the analysis of these flanking sequences in a statistically significant number (e.g. greater than one hundred, and more preferably greater than three hundred, and most preferably greater than five hundred) clinical isolates of a particlar bacterial or fungal species.

It is not intended that the present invention be limited by the technique by which the flanking sequences of such operons are analyzed. In one embodiment, primers directed to these sequences can be employed in an amplification reaction (such as PCR). On the other hand, these flanking sequences can conveniently be analyzed with restriction enzymes. Specifically, the present invention contemplates digesting bacterial or fungal DNA with one or more restriction enzymes which will produce a piece of nucleic acid of which at least a portion is outside (not bounded by) the 5' and 3' ends of the operon. For the convenience of detecting such digestion products by gel electrophoresis, it is preferred that the digestion product (due to the relatively limited resolution level of gel electrophoresis) be at least 200 bp in size (and more preferably between 400 and 30,000 bp in size).

In one embodiment, the present invention contemplates digestion of such DNA with restriction enzymes that cut only once in the DNA encoding 16S ribosomal RNA and only once in the DNA encoding 23S ribosomal RNA. In a preferred embodiment, the present invention contemplates digestion of bacterial DNA using a single restriction enzyme which cuts only once in the DNA encoding 16S ribosomal RNA and only once in the DNA encoding 23S ribosomal RNA.

In one embodiment, the present invention contemplates a method for vaccine development, comprising: a) providing a plurality of isolates of a single bacterial species, said isolates comprising DNA; b) examining said DNA from said isolates under conditions such that a phylogenetic tree is produced defining one or more phylogenetic subsets of said isolates; and c) evaluating a vaccine target antigen in said subset of isolates for variability.

In one embodiment, the present invention contemplates a method for vaccine development, comprising: a) providing a plurality (e.g. a panel) of clinical isolates of a single bacterial species; b) isolating bacterial DNA from each of said clinical isolates under conditions such that a DNA preparations is produced for each isolate, said DNA preparation comprising DNA flanking the DNA encoding 16S and 23S rRNA; c) digesting said DNA preparations with one or more restriction enzymes under conditions such that restriction fragments are produced, said restriction fragments comprising a digestion product for each of said isolates, said digestion product comprising a portion of said DNA encoding 16S rRNA or 23S rRNA and a portion of said DNA flanking said DNA encoding 16S rRNA or 23S rRNA; d) separating of said restriction fragments (e.g. by gel electrophoresis), e) detecting said digestion products of each of said isolates; f) grouping said isolates based on the number of digestion products having identical size to define one or more subsets of isolates; g) evaluating a vaccine target antigen in said subset of isolates for variability [e.g. examining the gene(s) encoding the antigen or the gene(s) encoding essential enzymes in the biosynthesis of the antigen].

It is not intended that the present invention be limited to the method by which the results are evaluated and grouped as set forth in step (f) above. A variety of types of phylogenic analysis can be employed. What is important is to use the phylogeny of the species of interest and look for antigen-encoding conserved genes that may be important in developing a vaccine.

It is not intended that the present invention be limited by the nature of the sample. The terms "sample" and "specimen" in the present specification and claims are used in their broadest sense. On the one hand they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, cells as well as solid tissue (including both normal and diseased tissue). These terms also refers to swabs and other sampling devices which are commonly used to obtain samples for culture of microorganisms.

It is not intended that the present invention be limited by the means of detection or the means of comparing digestion products. In one embodiment, said digestion products that are separated by gel electrophoresis are probed with a labeled oligonucleotide in a hybridization reaction.

It is not intended that the present invention be limited by the number of samples compared. A large number of clinical samples of a particular species are specifically contemplated within the scope of the present invention.

DEFINITIONS

To facilitate understanding of the invention, a number of terms are defined below. "Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

Prokaryotic ribosomes are constructed from 50S and 30S subunits that join together to form a 70S ribosome. The large subunit comprises a single "23S rRNA" molecule and a "5S rRNA" molecule, while the small subunit comprises a single "16S rRNA" molecule.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A."

Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

Ribosomal RNA molecules are characterized by the presence of numerous sequences that can form complementary base pairs with sequences located else where in the same molecule. Such interactions cause rRNA molecules to fold into three-dimensional configurations that exhibit localized double-stranded regions.

As used herein, the term "gene" means the deoxyribonucleotide sequences comprising the coding region and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The chromosomal DNA of prokaryotic cells contains multiple copies of the genes coding for rRNAs. For example, the bacterium E. coli ("EC") contains seven sets of rRNA genes. In the rRNA transcription unit of E. coli, the three genes are arranged in the order 16S-23S-5S, with "spacer" DNA separating each gene.

The terms "homology" and "homologous" as used herein in reference to nucleotide sequences and to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 $\mu$g/ml denatured salmon sperm DNA followed by washing in a solution comprising 5×SSPE, 0.1% SDS at 42° C. when a probe of about 500 nucleotides in length is employed.

Other equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency can be used (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl [see e.g., Anderson and Young, Quantitative Filter Hybridization, in *Nucleic Acid Hybridization* (1985)]. Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m-5°$ C. (5° C. below the $T_m$ of the probe) to about 20° C. to 25° C. below $T_m$. As will be understood by those of skill in the art a stringent hybridization can be used to identify or detect identical polynucleotide sequences or to identify or detect similar or related polynucleotide sequences.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction technologies well known in the art [Dieffenbach CW and GS Dveksler (1995) *PCR Primer, a Laboratory Manual*, Cold Spring Harbor Press, Plainview N.Y.]. As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification in PCR requires "PCR reagents" or "PCR materials", which herein are defined as all reagents necessary to carry out amplification except the polymerase, primers and template. PCR reagents nomally include nucleic acid precursors (dCTP, dTTP etc.) and buffer.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that it is detectable using any detection system including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence. Such enzymes can be used to create Restriction Fragment Length Polymorphisms (RFLPs). RFLPs are in essence, unique fingerprint snapshots of a piece of DNA, be it a whole chromosome (genome) or some part of this, such as the regions of the genome that specifically flank ribosomal RNA operons. All such RFLP fingerprints are indicative of the random mutations in all DNA molecules that inevitably occur over evolutionary time. Because of this, if properly interpreted, evolutionary relatedness of any two genomes can be compared based on the fundamental assumption that all organisms have had a common ancestor. Thus, the greater the difference in RFLP fingerprint profiles, the greater the degree of evolutionary divergence between them (although there are exceptions). With such an understanding, it then becomes possible, using appropriate algorithms, to covert RFLP profiles of a group of organisms (e.g. bacterial isolates) into a phylogenic (evolutionary) tree.

RFLPs are generated by cutting ("restricting") a DNA molecule with a restriction endonuclease. Many hundreds of such enzymes have been isolated, as naturally made by bacteria. In essence, bacteria use such enzymes as a defensive system, to recognize and then cleave (restrict) any foreign DNA molecules which might enter the bacterial cell (e.g. a viral infection). Each of the many hundreds of different restriction enzymes has been found to cut (i.e. "cleave" or "restrict") DNA at a different sequence of the 4 basic nucleotides (A, T, G, C) that make up all DNA molecules, e.g. one enzyme might specifically and only recognize the sequence A-A-T-G-A-C, while another might specifically and only recognize the sequence G-T-A-C-T-A, etc. etc. Dependent on the unique enzyme involved, such recognition sequences vary in length, from as few as 4 nucleotides (e.g. A-T-C-C) to as many as 21 nucleotides (A-T-C-C-A-G-G-A-T-G-A-C-A-A-A-T-C-A-T-C-G). From here, the simplest way to consider the situation is that the larger the recognition sequence, the fewer restriction fragments will result as the larger the recognition site, the lower the probability is that it will repeatedly be found throughout the genomic DNA.

In one embodiment, the present invention utilizes the restriction enzyme called EcoRI which has a 6 base pair (nucleotide) recognition site; Thus, given that there exist but 4 nucleotides (A,T,G,C), the probability that this unique 6 base recognition site will occur is $4^6$; or once in every 4,096 nucleotides. Given that the *H. influenzae* ("Hi") genome (chromosome) is approximately $2 \times 10^6$ bp (base pairs) in length, digestion of this DNA with EcoRI theoretically should yield 488 fragments. This varies significantly from isolate to isolate of *H. influenzae* because of "random mutations" that inevitably occurs over evolutionary time, some of which either destroy an EcoRI sequence cutting site, or create a new one. As such, the degree of variation in EcoRI RFLP profiles among a series of isolates within a given species such as *H. influenzae*, is indicative of the degree of genetic relatedness of these isolates (although there are exceptions). Using appropriate algorithms, such RFLP profiles are readily converted to "phylogenetic trees" which are simply a diagrammatic figures indicating the evolutionary divergence of isolates from some theoretically common ancestor.

Once the genomic (chromosomal) DNA of a bacterial isolate has been isolated, it is then digested (cut) with an enzyme such as EcoRI. Following the digestion, the resultant individual fragments are separated from one another based on their sizes. This can be done by using agarose gel electrophoresis. In essence, during electrophoresis the smaller molecules (DNA fragments) move faster than larger one and thus the resultant separation is a gradient from the largest to the smallest fragments. These can easily be visualized as bands down the electrophoresis gel, from the top to the bottom with the smallest fragments bottom-most.

Using ribotyping methodology, DNA fragments involving the multiple (6 for the case of *H. influenzae*, 7 for the case of *E. coli*, etc) ribosomal RNA operons and the immediately flanking DNA sequences (genes) can be distinguished by hybridization of the resultant electrophoresis separated DNA fragments with a radioactively labeled ribosomal operon DNA probe. This then reduces the total number of visualized DNA fragments (predicted above to be approximately 488 restriction fragments) to those only including or immediately flanking the RNA operons, about 14 fragments in toto for *H. influenzae*. Nonetheless, because of inevitable random background mutation indicative of evolutionary time, with the exception of very recently evolved clones, every independent isolate of *H. influenzae* will have a variant EcoRI ribotype RFLP profile. And the more variant, the more distantly related will be any two isolates so compared.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual*, Cold Spring Harbor Press, N.Y., pp 9.31–9.58].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists [J. Sambrook, J. et al. (1989) supra, pp 7.39–7.52].

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonuclotide probe or RNA probe to detect DNA species complementary to the ribo probe used.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature.

As used herein, the term "purified" or "to purify" refers to the removal of undesired components from a sample.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables).

The term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which.are gram negative or gram positive.

"Gram negative" and "gram positive" refer to staining patterns with the Gram-staining process which is well known in the art [Finegold and Martin, Diagnostic Microbiology, 6th Ed. (1982), CV Mosby St. Louis, pp 13–15]. "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

DESCRIPTION OF THE DRAWINGS

FIG. 2 is an autoradiograph showing the EcoRI RFLPs of *H. influenzae* isolates from diverse sources, including the genomically sequenced strain Rd.

FIGS. 5A–5E schematically show the genes found in the 30,000 bp flank regions of the 6 Ribosomal RNA Operons of the genomically sequenced *H. influenzae* strain Rd.

FIGS. 6A–6D schematically show the genes found in the 30,000 bp flank regions of the 7 Ribosomal RNA Operons of the genomically sequenced *E. coli* strain MG 1655.

DESCRIPTION OF THE INVENTION

Figure 1:
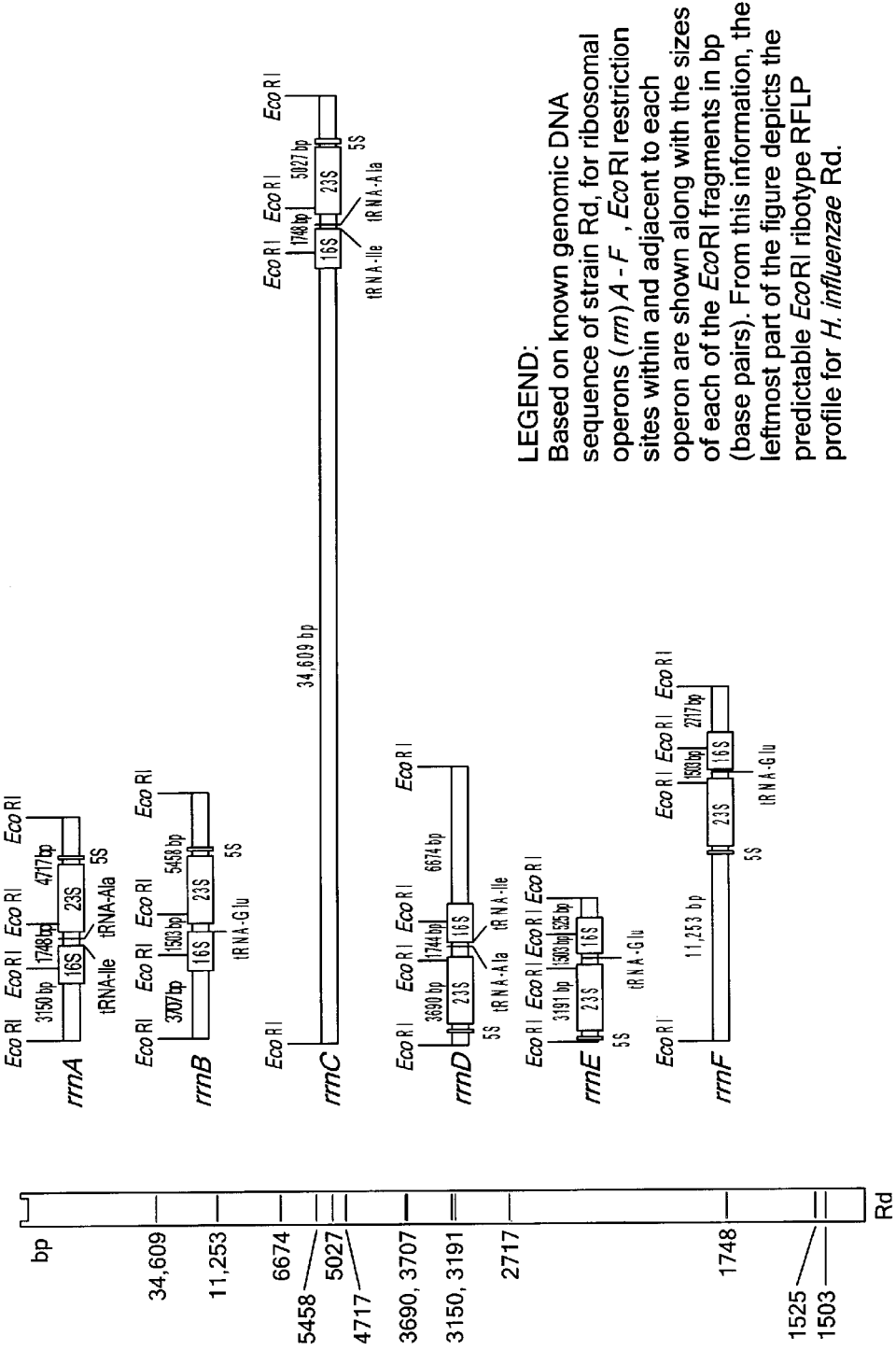
FIG. 1 schematically shows the 6 Ribosomal RNA Operons of the genomically sequenced *H. influenzae* strain Rd.

The present invention relates to the identification of groups within a species, and in particular, methods and compositions for determining a statistically significant number of different strains within a species of bacteria indicative of the species population structure as a whole in order to permit the evaluation of a vaccine target. The present invention contemplates the establishment of an initial phylogenic analysis of any bacterial pathogen of interest, for the purposes of subsequent analysis across the resultant evolutionary tree of that species for the variability of any potential antigen to be developed into a vaccine. With an accurate phylogenic picture of any particular species of bacteria, one skilled in the art of vaccine target evaluation can proceed with a rapid and inexpensive survey for variability of a large number of possible antigen vaccine target candidates, without resorting to "trial and error" with animal testing. This method, in effect, saves enormous time and expense otherwise involved with preliminary animal testing.

Important to understand is that the regions of the genomic DNA that flank (immediately adjacent) ribosomal RNA operons, for at least 30,000 bp (base pairs) to each side, are typically composed of contiguously linked neutral genes (see FIGS. 5 and 6). This can be seen analyzing the DNA that flanks the multiple copies of the 7 ribosomal operons found on the *E. coli* chromosome (see e.g. FIG. 3), and likewise for the chromosomes (genomes) of *H. influenzae* (see e.g. FIG. 1), and other bacterial species. The linkage of the multiple ribosomal RNA operons to neutral gene flank regions provides the molecular genetic basis of ribotyping. Neutral genes (also referred to as "housekeeping genes") typically code for enzymes involved in essential metabolic, catabolic, replicative functions and regulatory functions. While they are essential, they are nonetheless subject to normal, inevitable background rates of mutational changes in their DNA sequences. And unlike ribosomal operon genes (above), a significant number of such changes are tolerated. Because of this, such genes are in essence, molecular chronometers of evolutionary time.

It must be stressed that the polymorphisms currently exploited in conventional ribotyping are polymorphisms that are not directly related to ribosomal RNA operon sequences. Rather, because of the conservation of DNA encoding 16s and 23s rRNA within any species, polymorphisms relevant to ribotyping typically result from variation in closest flanking sequences (that is to say, nucleic acid falling outside of the region defined by: 5'-16S-spacer-23S-spacer-5S-3'). This point can be readily illustrated with the strain Hi Rd, because the complete chromosomal sequence of this strain is known. In this regard, it can be seen from FIG. 1 that it is possible to predict the precise size of the 12 different flank sequences generated by an EcoRI digestion (or the fragments generated with any other restriction enzyme for that matter) of the 6 rrn operons of strain Rd and likewise the genomically sequenced *E. coli* strain MG 1655 (see FIGS. 3 and 4). With such knowledge of the RFLP profile of the sequenced Hi strain Rd, using molecular genetic methods (such as hybridization), it is possible to precisely analyze any alterations from this prototypic ribotype fingerprint as found among other Hi isolates.

From this example with *H. influenzae*, it should be clear that the polymorphisms generated by the conventional ribotyping technique have nothing directly to do with Ribosomal RNA operon sequences. Rather, these polymorphisms result from variations in the neutral genes that are genetically-linked to (i.e. that flank) the multiple ribosomal RNA operons encoded by all bacterial chromosomes.

The present invention utilizes an initial phylogenic analysis (using such methodology as provided by ribotyping) as a means of grouping of strains within a species to approximate the minimum variability in any vaccine target. This permits the evaluation of the vaccine target in a more limited number of bacterial isolates. The description of the invention involves the I) Selection Of The Phylogenic Analysis, and II) Evaluating A Vaccine Target Antigen Following Phylogenic Analysis; and III) Automation.

I. Selection of the Phylogenic Analysis

It is not intended that the present invention be limited to only one type of phylogenic analysis. The phylogenic analysis of clinical isolates, regardless of the particular methodology employed, is contemplated as a pre-step to vaccine target antigen evaluation. In this manner, comparative intraspecies analysis of the genetic relatedness of any collection of isolates of the same bacterial or fungal species can be exploited for phylogenic (evolutionary) analysis to select for conserved antigen-encoding genes potentially useful for vaccine development. This can be accomplished by any number of methods, including but not limited to: i) indirectly, using MLEE (multi locus enzyme electrophoresis); ii) directly, by comparative DNA sequencing; (iii) directly, by ribotype associated RFLP analyses; (iv) directly, by PFGE (pulse field gel electrophoresis)-resolved RFLP analysis; and (v) directly, by PCR-based amplification of chromosomal polymorphisms (e.g. RAPD, random amplified polymorphic DNA analysis).

II. Evaluating a Vaccine Target Antigen Following Phylogenic Analysis

Vaccine target antigens contemplated by the present invention should be accessible to host immune mechanisms (e.g. accessible to antibody) in vivo and capable of eliciting protective immunity without causing adverse side effects. On the basis of these two initial criteria, each pathogenic microbe will present with several potential candidate molecules that might be developed into a successful vaccine. However, the present invention permits selection using a third criteria, namely selection among these potential candidates based on an evaluation of each candidate molecule within the groupings generated by phylogenic analysis.

In this regard, the present invention employs a method comprising the grouping of strains within a species to approximate the minimum variability in any vaccine target. That is to say, the method of the approach only provides a baseline of variability for a particular vaccine target. Because vaccine targets that are surface antigens (e.g. surface proteins) are under more pressure to vary, an evaluation of the target antigen following phylogenic analysis may reveal additional variability.

Ideally, the candidate vaccine target molecule should have conserved epitope(s) in the subset(s) of isolates grouped by the phylogenic analysis of the present invention. This can be readily evaluated by selecting an isolate from each of the groups (e.g. subsets) and evaluating the variability of the candidate molecule in the isolate (which is representative of the subset).

It is not intended that the present invention be limited to a particular approach to the evaluation of variability of the candidate vaccine antigen. In one embodiment, key genes (e.g. genes encoding the candidate antigens or an enzyme essential to the biosynthesis of the antigen) can be evaluated by PCR to determine whether or not they are conserved. In another embodiment, where the antigen is a protein (or glycoprotein) antigen, variability can be examined in the primary amino acid sequence of the candidate molecule. Sequence alignment computer programs which are commerically available will permit the comparison of the primary amino acid sequence (or at least a portion thereof) of the candidate molecule for each subset in order to determine whether the molecule contains a conserved epitope (or epitopes) to which antibody can be directed. Ideally, the candidate molecule will have such a conserved epitope (or epitopes) for approximately 80–100% of the isolates tested (i.e. the representative isolates from the groups identified through phylogenic analysis). With the epitope present in all isolates tested, there is the potential for approximately 80–100% coverage in the vaccine for the particular species of pathogenic bacteria.

A further consideration can also be applied to vaccine design. Specifically, it is desirable to target vaccines to disease causing, but not harmless (commensal) strains of the species. If the latter strains are targeted by a vaccine, their eradication may actually be harmful through the phenomenon of competitive exclusion. In one embodiment, conserved epitopes are selected that do not appear in the candidate molecules in commensal isolates.

Finally, even where an antigen has been selected without the benefit of phylogenic analysis, one can evaluate the efficacy of the antigen using the phylogenic strategy (e.g. the phylogenenic tree of a species representing the diversity of the species). For instance, an antibody could be evaluated for the degree of reactivity across the species by selecting representative isolates from the major lineages (or all the isolates in the tree) and testing the antibody.

III. Automation

The present invention contemplates the automation of analysis. In this regard, the present invention specifically contemplates the utilization of the Qualicon (a Dupont subsidiary) "RiboPrinter System"—which is a fast automated apparatus that is (with some modifications, including but not limited to, improvement in the overall descriminatory power, i.e. the size range of the fragments that can be resolved) amenable to the automation of some of the above-described methods. In operation, single colonies from 8 unknown microbes are inoculatd directly into a sample carrier into which a "DNA pre pack" is added that contains lysis buffer (enzymes to break open bacteria, along with restriction endonucleases for cutting genomic DNA, along with marker DNA molecules for comparative sizing of RFLP profiles).

After initial heat inactivation of colonies, followed by cell lysis and restriction of the DNA, the DNA is then automatically extracted and restriction fragments separated according to size by gel electrophoresis, and then transferred to a hybridization membrane. DNA is then automatically hybridized to a labeled ribosomal RNA operon probe, after which a chemiluminescent agent is introduced. Emission of light from hybridized fragments is captured by digitizing camera and stored as image data. Using proprietary algorithms, a RiboPrint pattern for each sample is extracted from the image data. This pattern can then be compared to other RiboPrint RFLP profiles stored in the system. Such results can be generated every 8 hours, with analysis of the next set of 8 samples begun 2 hours after the first.

The present invention also contemplates a new means for resolving species specific ribosomal RNA bands. This involves hybridization in solution following restriction digestion of the unknown chromosomal DNA sample after which unbound chemiluminescent probe is removed and the sample is electrophoresed. At this point, based on the known rate of migration of DNA fragments of variant size, a chemiluminescent detector is used to detect when hybridized restriction fragments chemilumiescently labeled with the rrn probe elute from the electrophoretic gel. Given the elution rate will be determined by speed of migration, and that migration speed for a fragment of a given size is predictable, the time at which the so chemilumiescently labeled hybridized fragment elutes will indicate its size and thus reveal the signature bands indicative of one species or another.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); bp (base pair); CPM (counts per minute).

Figure 9:
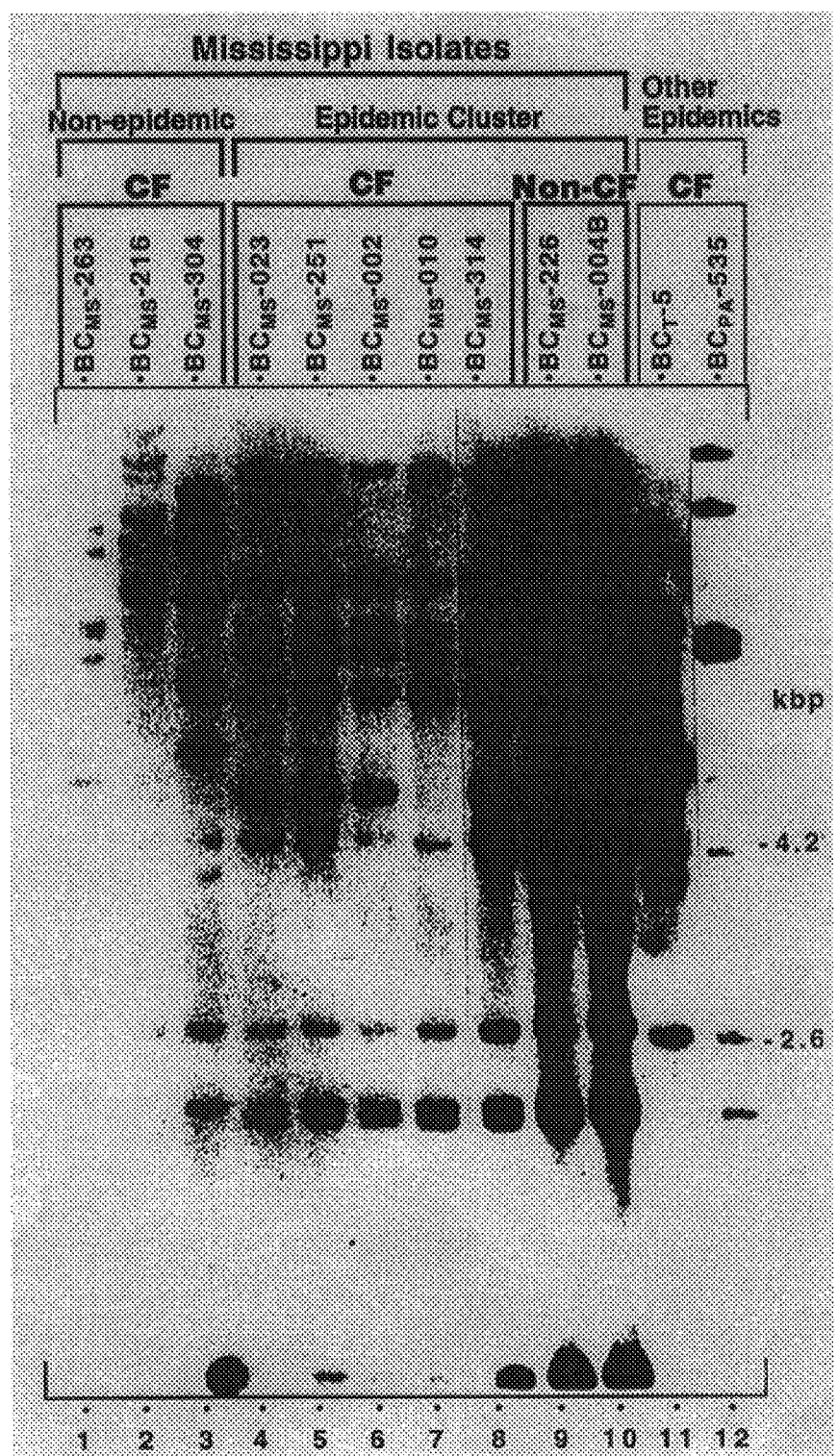
FIG. 9 is an autoradiograph of detected *P. cepacia* RFLP fragments separated by gel electrophoresis.
Figure 10:
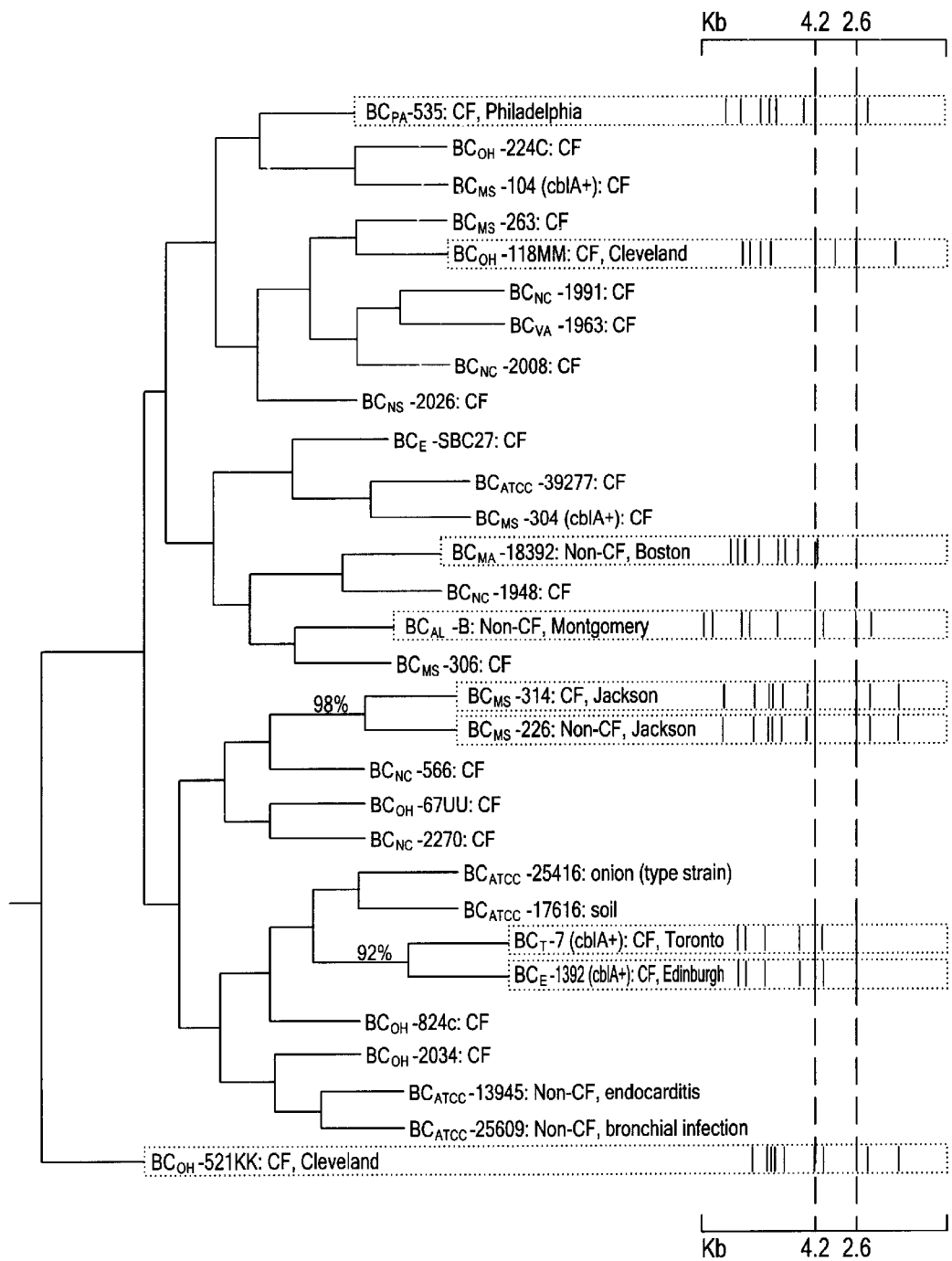
FIG. 10 is a dendrogram (i.e., a phylogenetic tree) of a diverse collection of *B. cepacia* isolates from various clinical, geographical and environmental sources.

In one embodiment, the method steps for preparing a phylogenically classifed tree comprise: 1) collection of statistically significant number of isolates of given species of interest, typically ca. 400–800 or more individual strains from diverse clinical sources, geographical locales and time span; 2) growth, and then storage of all isolates at –80° C.; 3) chromosomal DNA isolation (CsCl) equilibrium density gradient centrifugation for each isolate; 4) restriction endonuclease digestion of chromosomal DNA of each isolate; 5) electrophoretic separation of digested chromosomal DNA of each isolate; 6) transfer of chromosomal DNA fragments to nitrocellulose membranes; 7) isolation and preparation of isotopically-labelled rrn (ribosomal RNA operon) probes; 8) isotopically-labelled rrn probing (hybridization) of membranes containing the chromosomal restriction fragments; 9) autoradiography of probed membranes (see e.g. FIGS. 2, 4, 9); 10) computer analysis of autoradiographs (RFLP profiles); 11) computer-based construction of phylogenetic trees based on autoradiograph RFLPs (see FIGS. 7, 8, 10); 12) analysis of resultant tree with respect to independent phenotypic variables and known genomic sequence of one isolate of the involved species.

It is not intended that the present invention be limited to the nature of the computer analysis or the computer-based construction of phylogenetic trees. The rrn-based polymorphisms can be scanned using a Stratagene Eagle Eye system, and entered into a computerised database (Scanalytics/CSPI). For rrn RFLPs, a shared ribotype would correspond to an index of similarity, D$\geq$0.790.

The ribotype RFLPs generated can be entered into the database and used in further phylogenic analysis. Initial, primary output of a ribotype analysis can comprise of autoradiographs of ribotypes, or Polaroid-type photos of UV-activated, EthBr- stained, PFGE-resolved chromosomal DNA fragments respectively. Because of inherent variations in both intensity and sharpness of resolved bands of DNA, interpretation of raw data at this level is time consuming and subjective. However, with video scanning and computerised data interpretation these RFLP fingerprint patterns may be translated into bar-code format. The unambiguous standardized bar-code format is easily interpretable, readily stored in a computer memory, and allows for the rapid comparison of bar-coded chromosomal fingerprints of large numbers of bacterial strains.

Phylogenic relationships among the isolates can be examined with the neighbour-joining (NJ) method of Saitou and Nei, "The neighbor-joining method: A new method for reconstructing phylogenetic trees," *Mol. Biol. Evol.* 4:406–425 (1987). From rrn patterns, the pairwise genetic distances among strains can be used as the input distance matrix. Confidence intervals on the tree topology can be estimated by bootstrapping analysis. See e.g. J. Felsenstein J, "Confidence limits on phylogenies: an approach using the bootstrap," *Evolution* 39:783–791 (1985).

In a preferred embodiment, the ribotyping results can be converted, using RFLPscan software (Scanalytics) into a 27-character 0/1 string (2% match tolerance). The data from each experiment can be entered into a data base. The 0/1 strings are used to estimate genetic distances with the algorithm $Gd_{xy}=(N_x+N_y)/(N_x+N_y+N_{xy})$. A tree topology can be inferred with the distance matrix analysis UPGMA (unweighted pair group method using arithmetic averages) and the final dendrogram generated with TreeCon software.

EXAMPLE 1

Phylogenic Analyis of *H. influenzae*

Availability of the complete sequence of the chromosome of the *Haemophilus influenzae* ("Hi") strain Rd allowed us to predict a priori the resultant EcoRI RFLP profile generated from the known 6 rrn (ribosomal RNA operon) of this strain. As shown in FIG. 1, with EcoRI sites occurring once each, in species-conserved 16s and 23s rrn gene sequences of each rrn operon, two possible internal fragments (16s-spacer-23s) are generated depending on presence or 1 or 2 tRNA sequences within the spacer region between 16s and 23s genes. Among the >400, putative typable and "NT" (non-typable, i.e. unencapsulated) Hi isolates examined by EcoRI ribotyping, all serotype "a" through "e" RFLP profiles and 253of 311 NTHi (non-typable Hi) RFLP profiles contained both signature bands. 53 NTHi RFLP profiles lacked both signature bands, whereas four lacked the 1748 bp signature band and 1 lacked the 1503 bp-signature band. All serotype "f" RFLP profiles lacked both signature bands (representative data is shown in FIG. 2). These 58 NT and 8 serotype f isolates lacking EcoRI ribotype signature bands appear not to be members of the species *H. influenzae* but appear to be a new subspecies or species.

Figure 7:
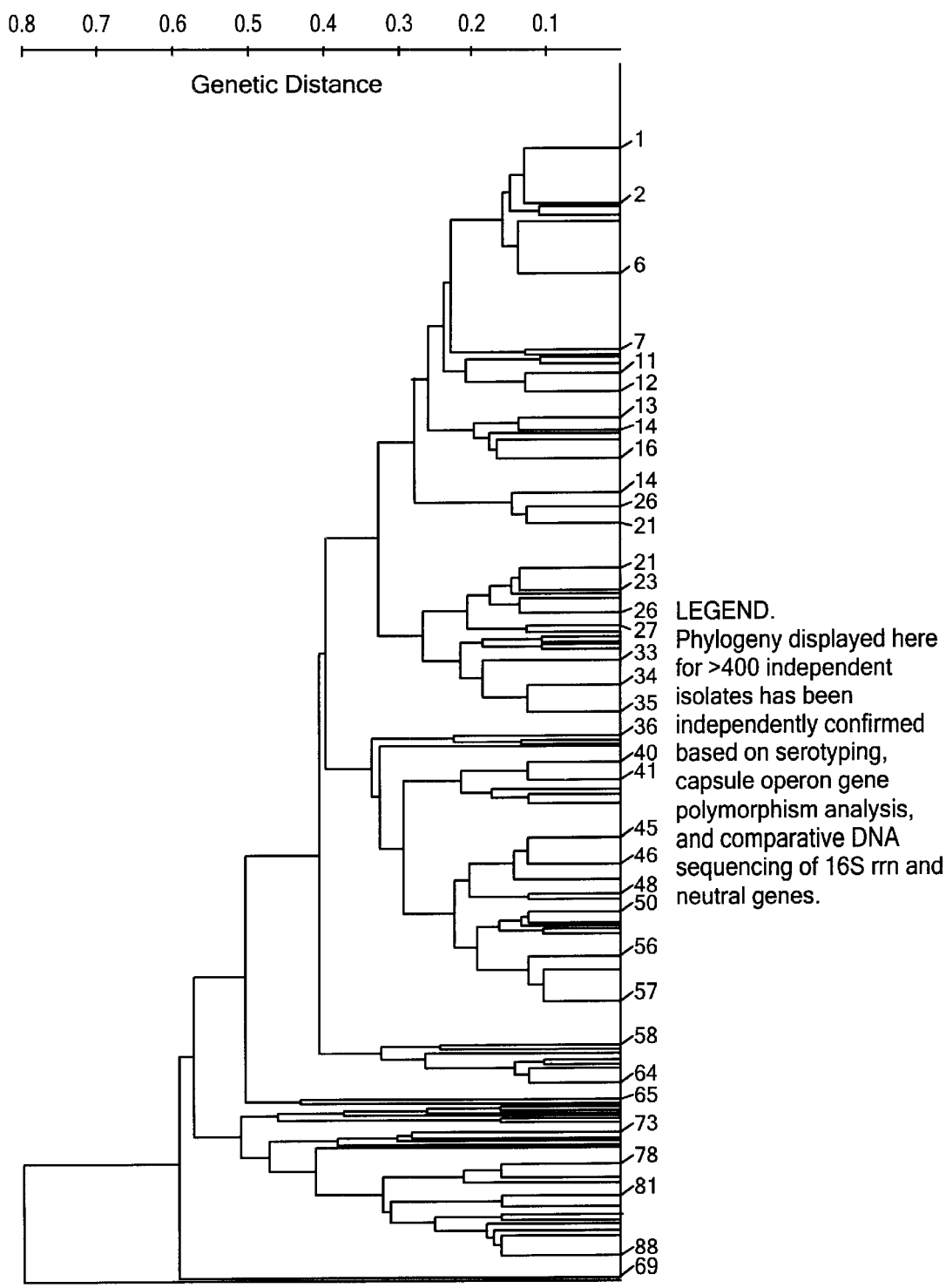
FIG. 7 is a dendrogram (i.e., a phylogenetic tree) of a diverse collection of *H. influenzae* isolates (type a–f, and non-typable) from various clinical, geographical and environmental sources.
Figure 8A:
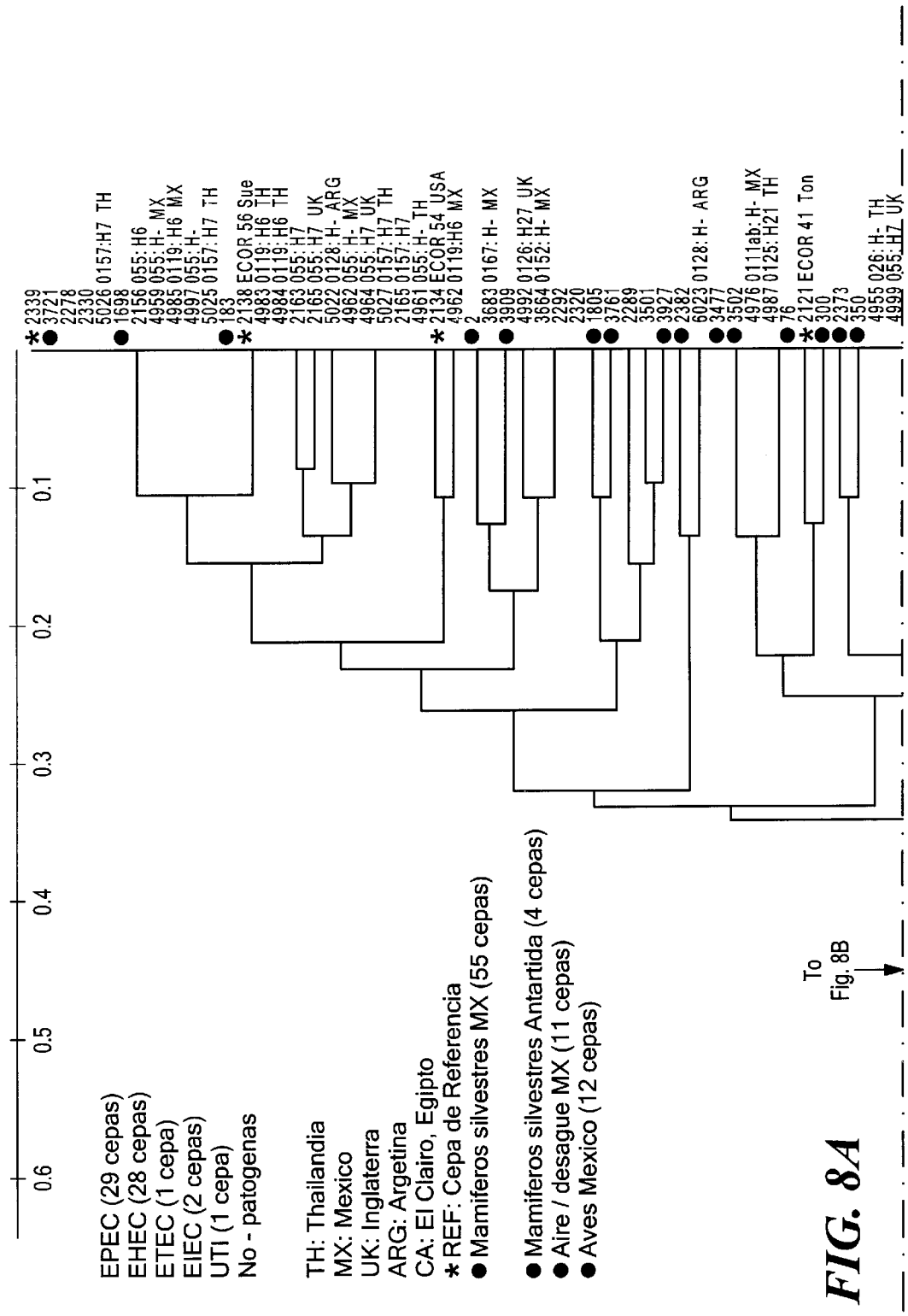
FIGS. 8A–8D represent a dendrogram (i.e., a phylogenetic tree) of a diverse collection of *E. coli* isolates from various clinical, geographical and environmental sources.
Figure 8B:
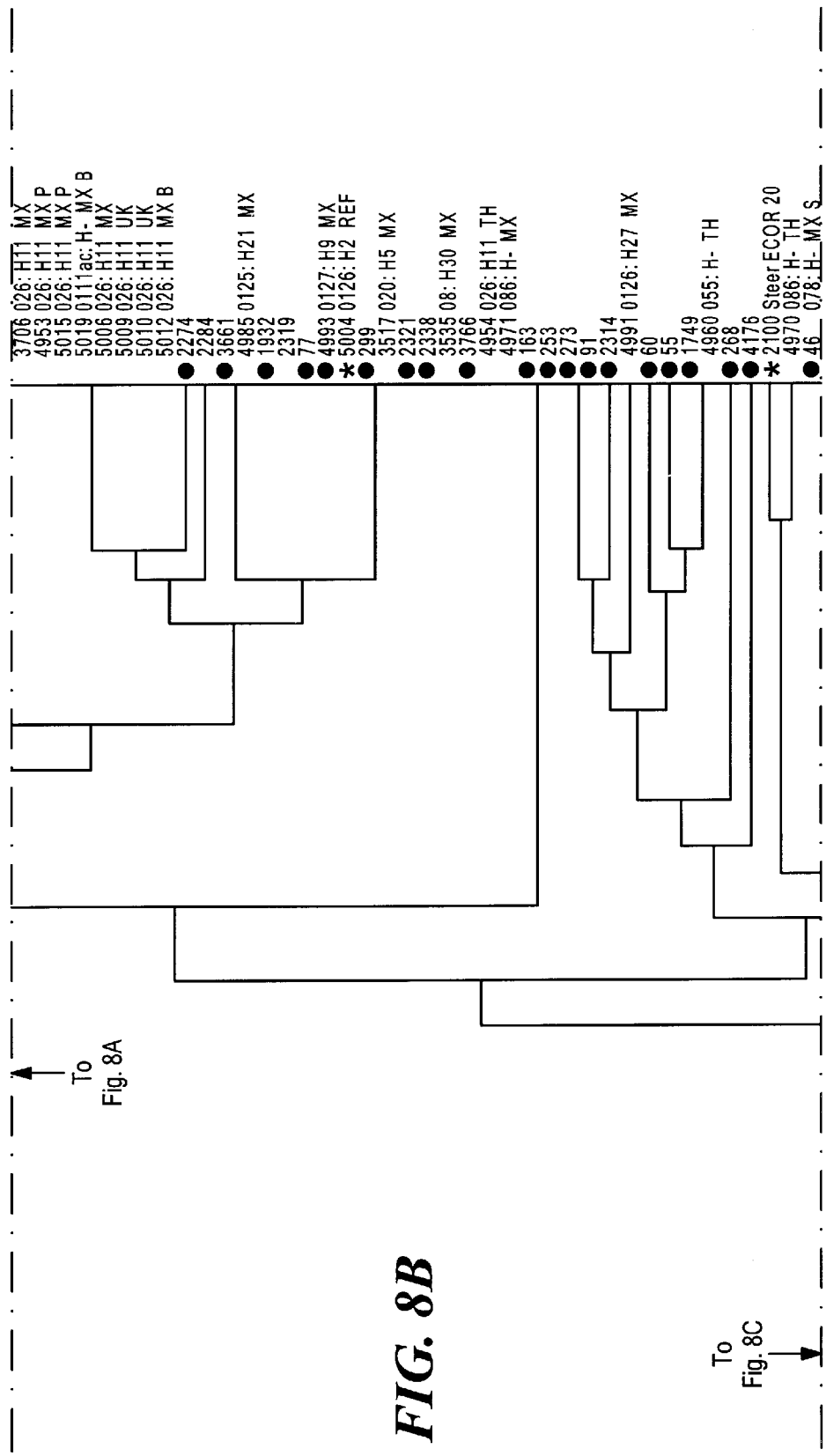
Figure 8C:
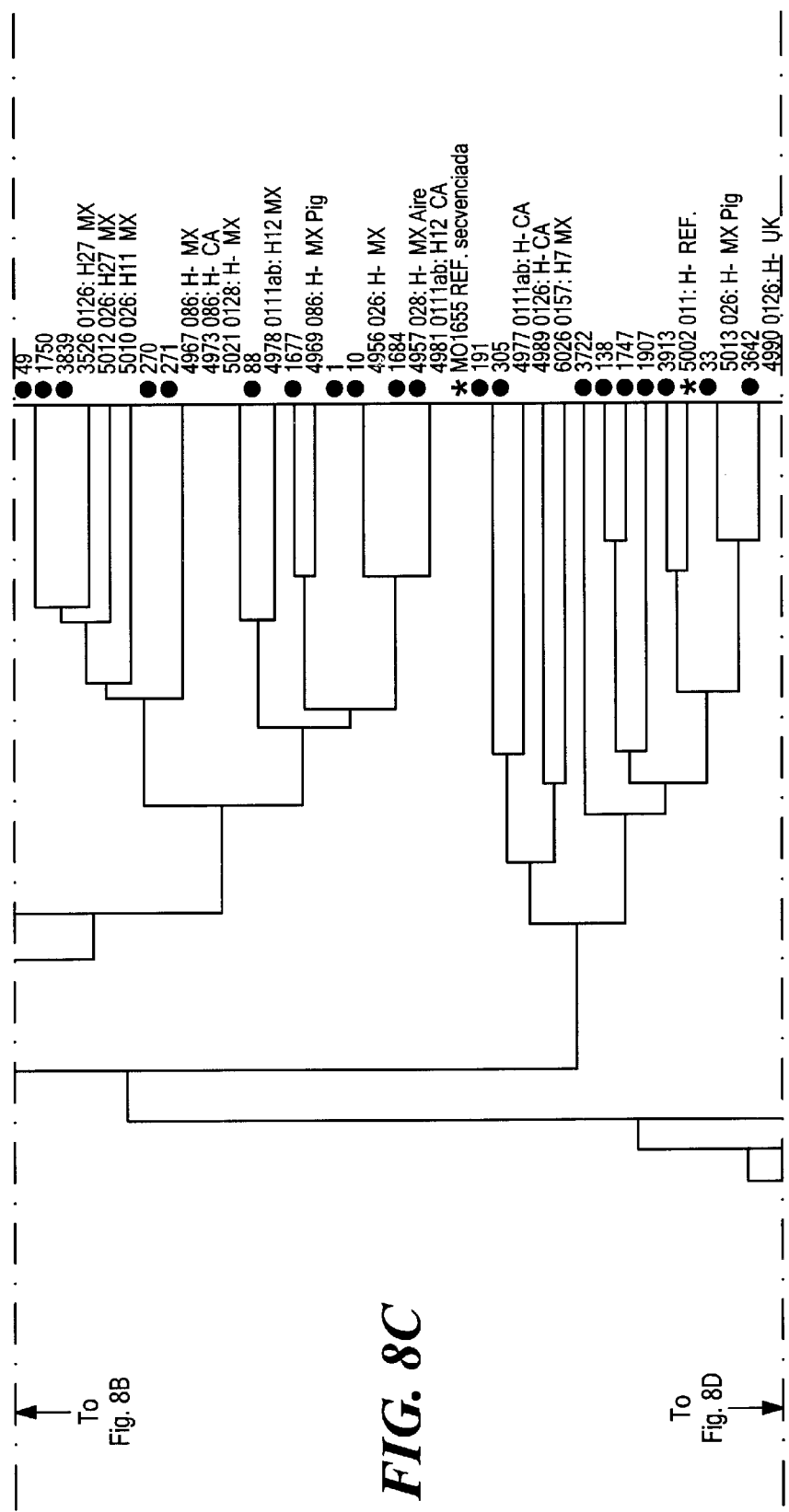
Figure 8D:
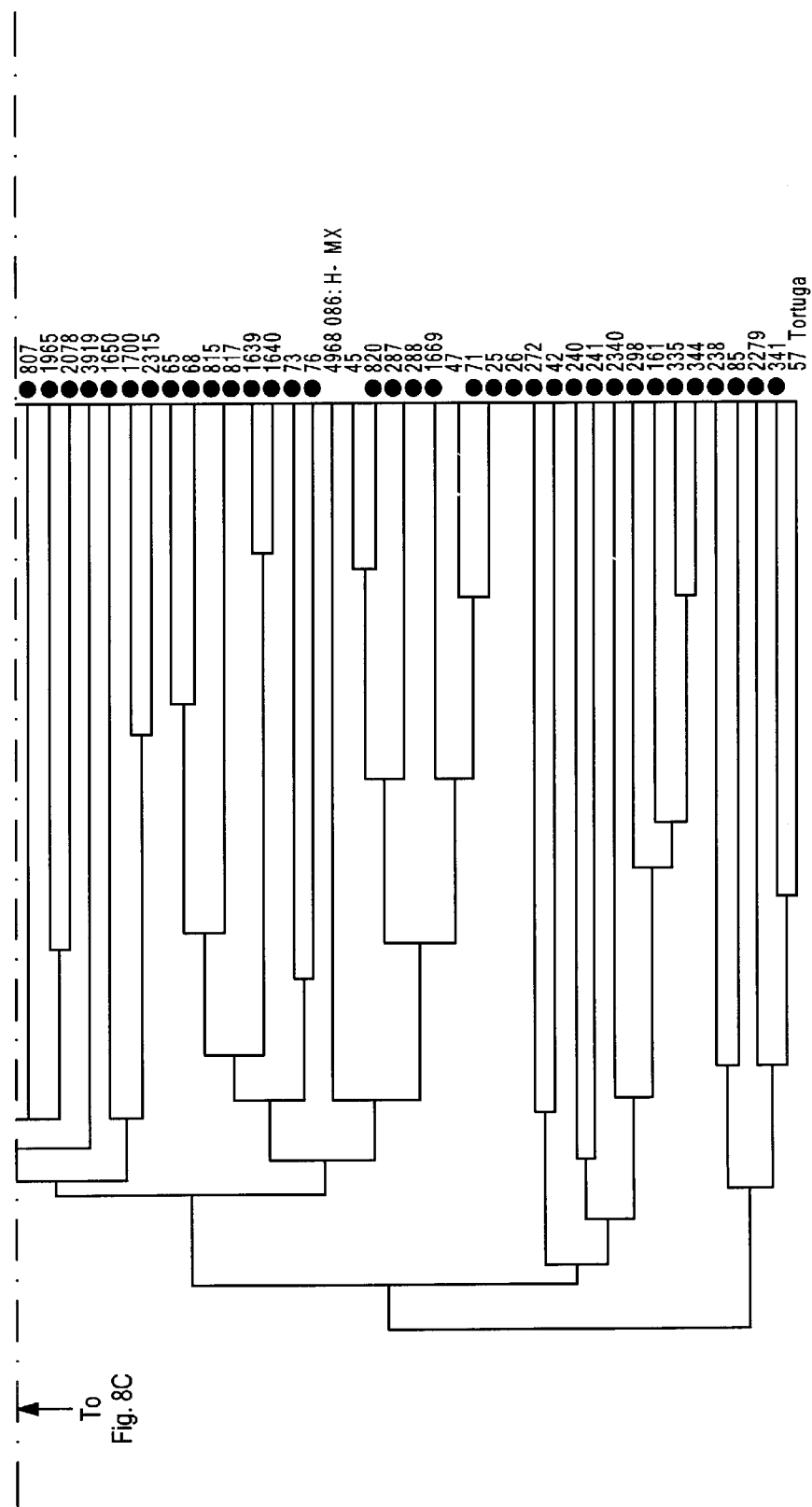

As described above, all 8 serotype "f" isolates plus 55 of 58 NTHi Isolates lacking one or more species specific EcoRI signature bands appear clustered together in the FIG. 7 dendrogram (the phylogenic tree) as a clearly distinct lineage(s) from all of the other EcoRI signature band-containing isolates, both serotype "a" through "e" and NT. Based on methods known in the art, such as multi-locus enzyme electrophoresis (MLEE), this was not revealed in previous phylogenetic analyses of *H. influenzae*. Preliminary 16s rrn gene sequencing has confirmed that putative Hi isolates missing the EcoRI ribotype species-specific signature band(s) appear to have been mistyped as Hi by clinical microbiology labs providing these isolates.

The grouping of the isolates into subsets of *H. influenzae* clinical isolates, permits the evaluation of a candidate vaccine antigens for this species (using the approaches described above). The phylogenic analysis for *H. influenzae* provides the minimum number of isolates (i.e. representative isolates) to be tested.

EXAMPLE 2

Phylogenic Analyis of *E. coli*

Figure 3:
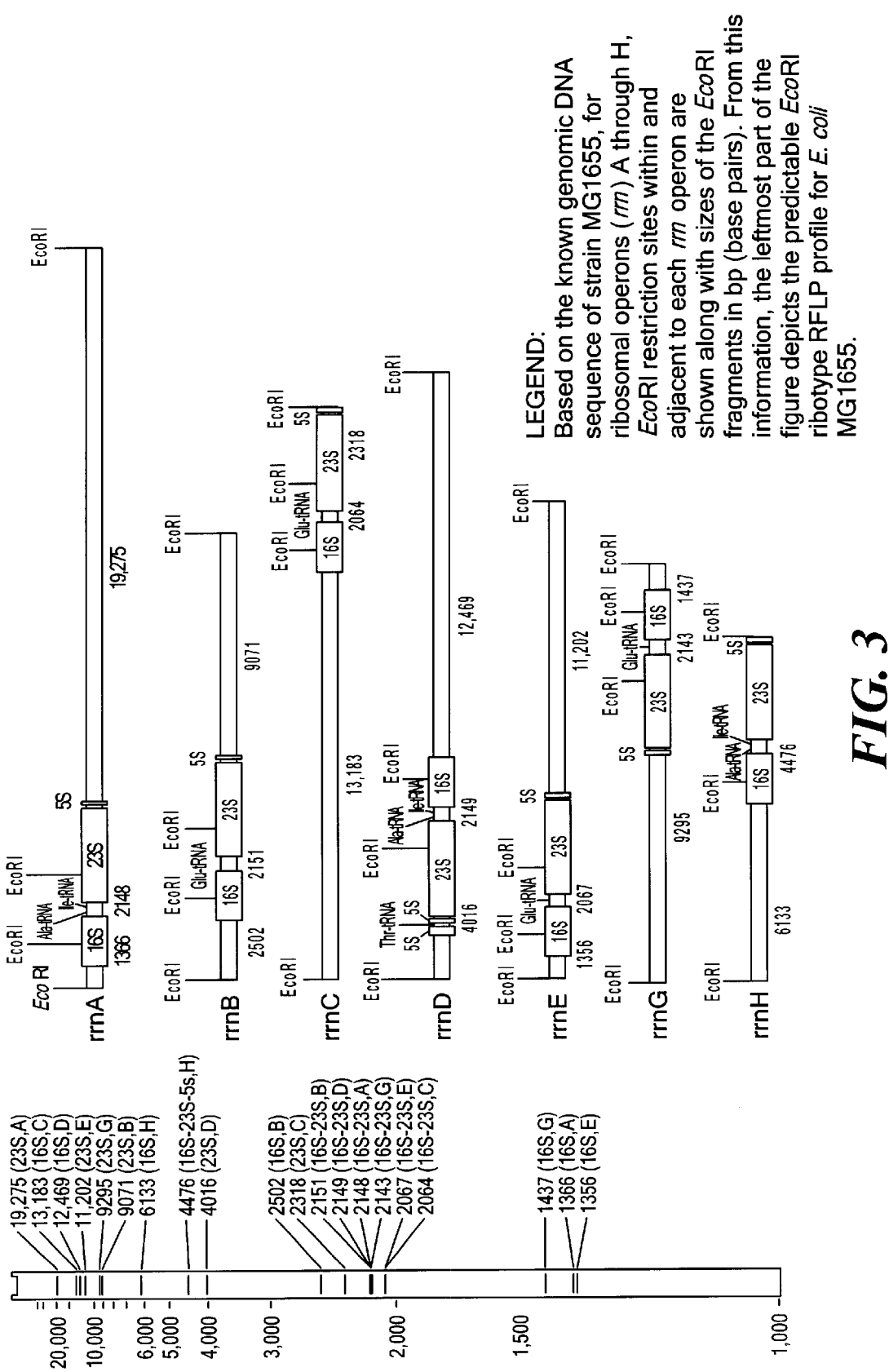
FIG. 3 schematically shows the 7 Ribosomal RNA Operons of the genomically sequenced *E. coli* strain MG 1655.
Figure 4:
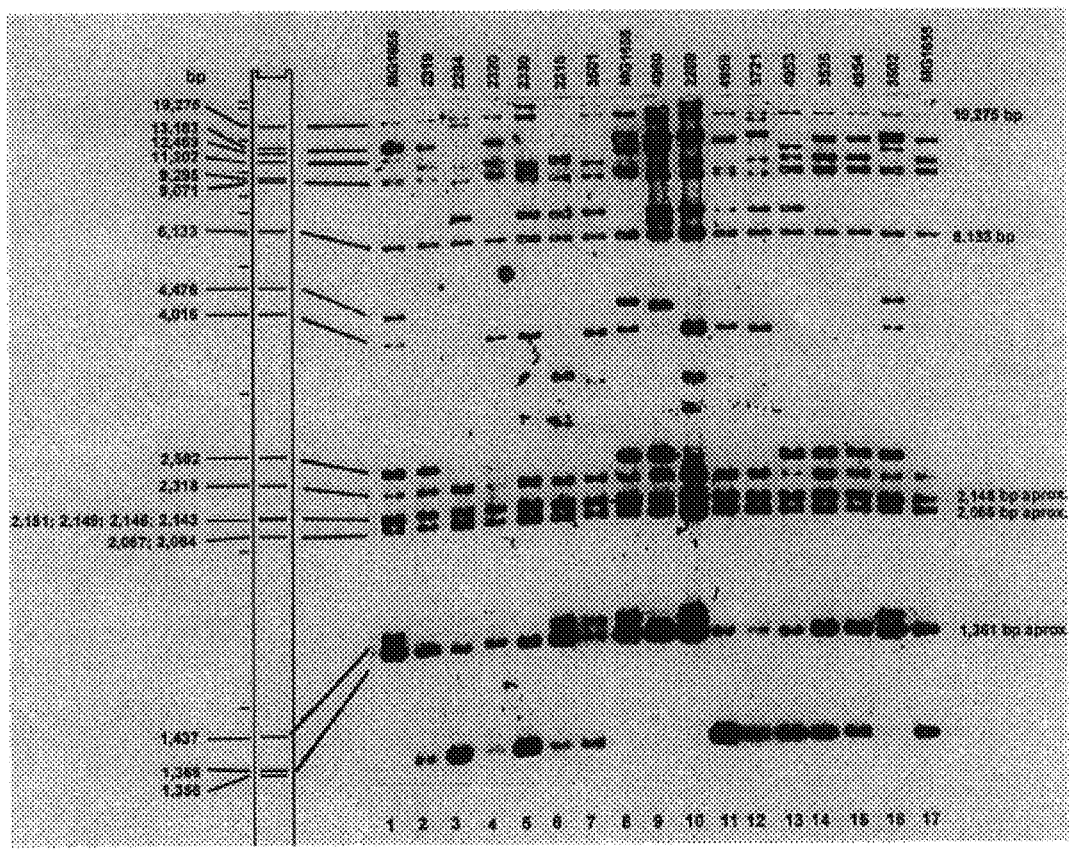
FIG. 4 is an autoradiograph of EcoRI RFLPs of *E. coli* isolates from diverse sources, including the genomically sequenced strain MG 1655.
Figure 5B:
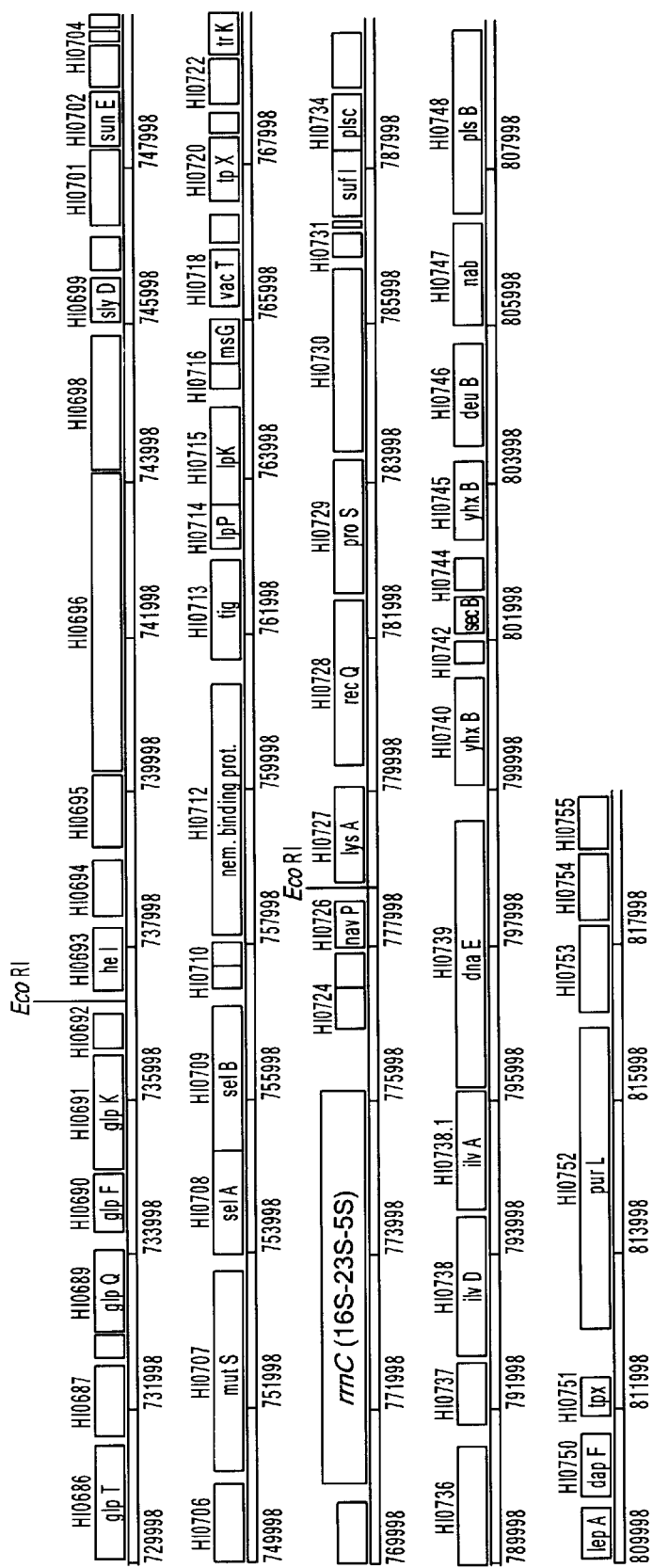
Figure 5C:
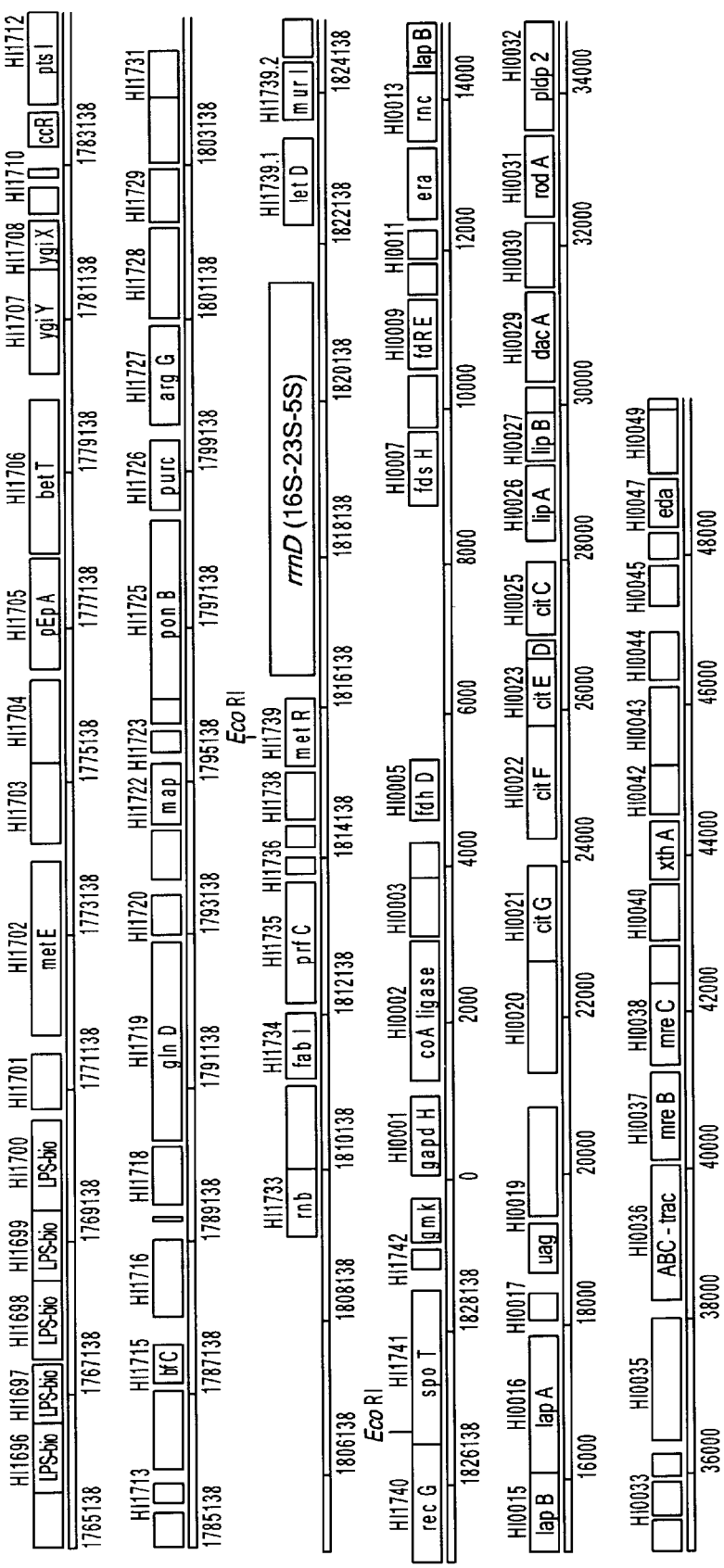
Figure 5D:
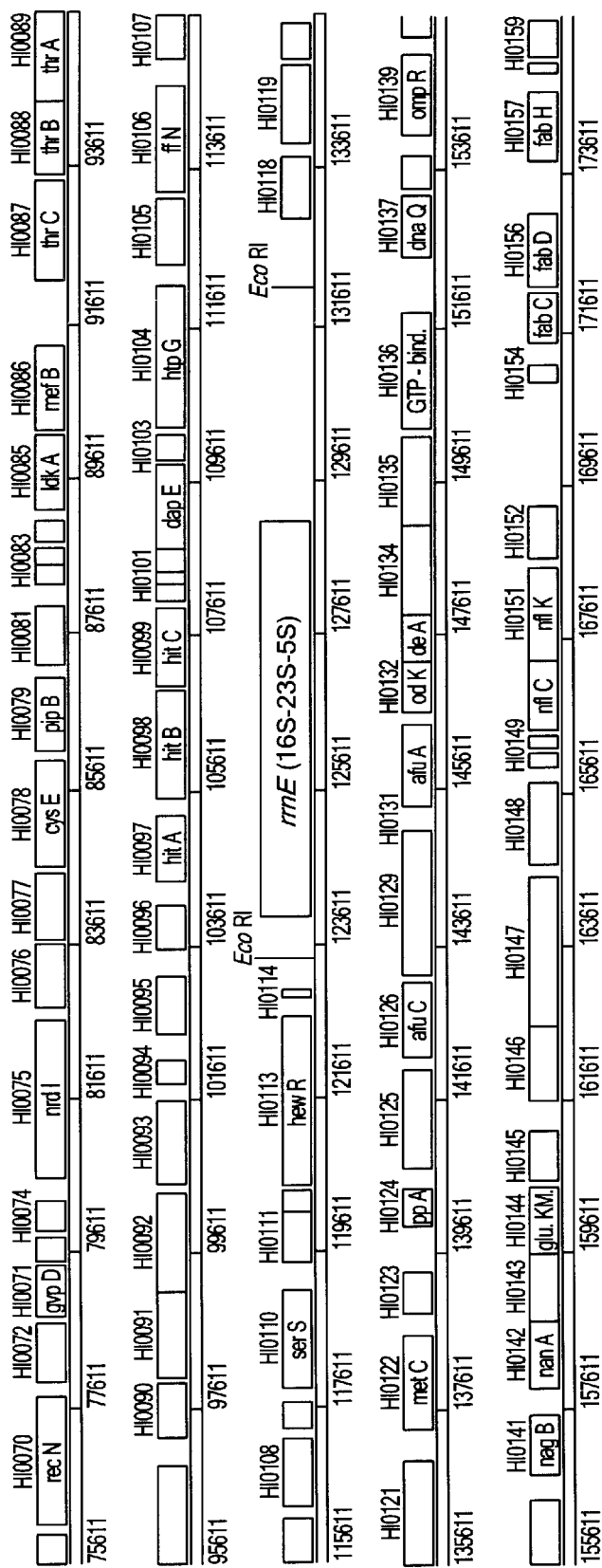
Figure 5E:
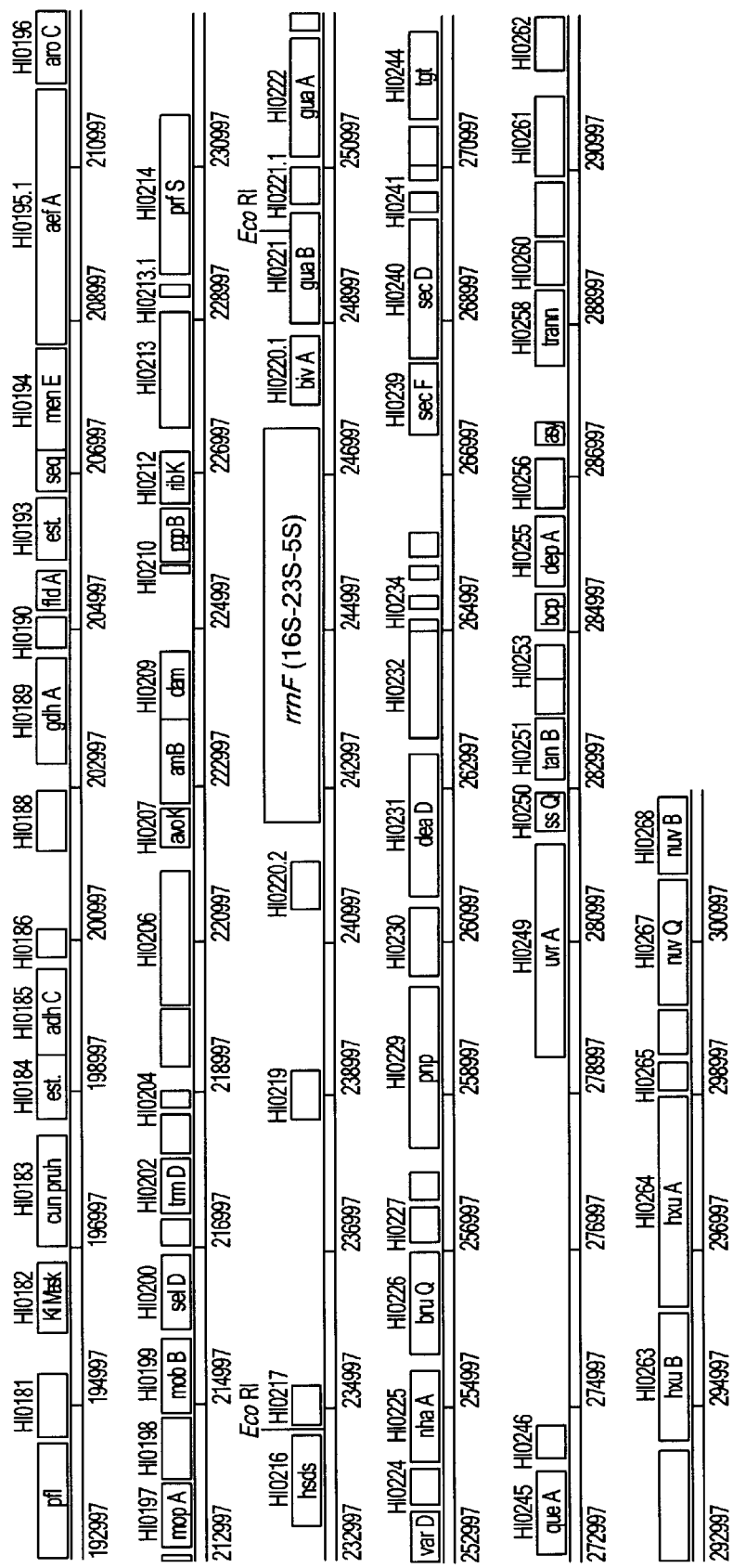

Availability of the genomically sequenced *E. coli* strain MG 1655 allowed us to predict a priori the resultant EcoRI RFLP profile generated from the known 7 rrn (ribosomal RNA operon) of this strain (FIG. 3). Clinical isolates of *E. coli* were examined by EcoRI ribotyping methodology (FIG. 4). Based on the RFLP patterns, Isolates were clustered together in a dendrogram (the phylogenic tree) in clearly distinct lineages (FIG. 8). The grouping of the isolates into subsets (i.e. lineages) of *E. coli* clinical isolates, permits the evaluation of a candidate vaccine antigens for this species (using the approaches described above). The phylogenic analysis for *E. coli* provides the minimum number of isolates (i.e. representative isolates) to be tested.

EXAMPLE 3

Phylogenic Analysis of *P. cepacia*

*Burkholderia cepacia* is an important pathogen in cystic fibrosis (CF) and an infrequent cause of nosocomial infection in non-CF patients. Restriction fragment length polymorphism (RFLP) profiles of clinical isolates were analyzed (FIG. 9), a ribotype-based phylogenic tree (FIG. 10) was constructed. The results indicate a single dominant clone was found in both CF and non-CF groups. Phylogenic analysis suggests that it has evolved independently, and that such highly transmissible strains can emerge rapidly and randomly. The grouping of the isolates permits the evaluation of a candidate vaccine antigens for this species (using the approaches described above).

Acronyms of the genes comprising the 30,000 bp flanks of the ribosomal RNA operons of the genomically sequenced *H. influenzae* strain Rd.
rrnA and rrnB flanks

| | |
|---|---|
| ABC transporter, ATP-binding protein (HI0621) | |
| ABC transporter, ATP-binding protein (HI0658) | |
| ABC transporter, ATP-binding protein (HI0664) | |
| arcB | ornithine carbamoyltransterase (HI0596) |
| arcC | carbamate kinase (HI0595) |
| aroE | shikimate 5-dehydrogenase (HI0655) |
| asd | aspartate-semialdehyde dehydrogenase (HI0646) |
| asnA | aspartate--ammonia ligase (HI0564) |
| bisC | biotin sulfoxide reductase (HI0643) |
| coaA | pantothenate kinase (HI0631) |
| cpdB | 2',3'-cyclic-nucleotide 2'-phosphodiesterase (HI0583) |
| crcB | crcB protein (HI0598) |
| cyaA | adenylate cyclase (HI0604) |
| cydD | ATP-binding transport protein (HI0663) |
| cysE | serine acetyltransferase (HI0606) |
| def | polypeptide deformylase (HI0622) |
| dod | ribulose-phosphate 3-epimerase (HI0566) |
| fkpA | FkbP-type peptidyl-prolyl cis-trans isomerase (HI0574) |
| fmt | methionyl-tRNA formyltransferase (HI0623) |
| folD | methylenetetrahydrofolate dehydrogenase/ methenyltetrahydrofolate cyclohydrolase (HI0609) |
| fucA | L-fuculose phosphate aldolase (HI0611) |
| fucI | L-fucose isomerase (HI0614) |
| fucK | fuculokinase (Hl0613) |
| fucP | L-fucose permease (HI0610) |
| fucR | L-fucose operon activator (HI0615) |
| fucU | fucose operon protein (HI0612) |
| fusA | elongation factor G (HI0579) |
| gidA | glucose inhibited division protein (HI0582) |
| glmU | UDP-N-acetylglucosamine pyrophosphorylase (HI0642) |
| glp | glp protein, putative (HI0618) |
| glpR | glycerol-3-phosphate regulon repressor (HI0619) |
| gph | phosphoglycolate phosphatase (HI0565) |
| gpsA | glycerol-3-phosphate dehydrogenase (NAD+) (HI0605) |
| greB | transcription elongation factor (HI0569) |
| gyrB | DNA gyrase, subunit B (HI0567) |
| hemoglobin-binding protein (HI0635) | |
| hemoglobin-binding protein (HI0661) | |
| hemX | uroporphyrin-III C-methyltransferase (HI0603) |
| hemY | hemY protein (HI0602) |
| hepA | ATP-dependent helicase (HI0616) |
| hlpA | 28 kDa outer membrane protein (HI0620) |
| hydrolase (HI0584) | |
| kdtA | 3-deoxy-d-manno-octulosonic-acid transferase (HI0652) |
| kdtB | lipopolysaccharide core biosynthesis protein (HI0651) |
| lipopolysaccharide biosynthesis protein (HI0653) | |
| mclA | sigma-E factor negative regulatory protein (HI0629) |
| mdaB | modulator of drug activity B (HI0648) |
| mscL | large conductance mechanosensitive channel (HI0626) |
| N-carbamyl-L-amino acid amidohydrolase (HI0588) | |
| oxyR | hydrogen peroxide-inducible genes activator (HI0571) |
| pepE | peptidase E (HI0587) |
| pldB | lysophospholipase L2 (HI0645) |
| potE | putrescine-ornithine antiporter (HI0590) |
| purB | adenylosuccinate lyase (HI0639) |

Acronyms of the genes comprising the 30,000 bp flanks of the ribosomal RNA operons of the genomically sequenced *H. influenzae* strain Rd.
rrnA and rrnB flanks

| | |
|---|---|
| recA | recA protein (HI0600) |
| recX | regulatory protein (HI0599) |
| rep | ATP-dependent DNA helicase (HI0649) |
| rpoE | RNA polymerase sigma-E factor (HI0628) |
| rpL7/L12 | ribosomal protein L7/L12 (HI0641) |
| rpL10 | ribosomal protein L10 (HI0640) |
| rps12 | ribosomal protein S12 (HI0581) |
| rpS7 | ribosomal protein S7 (HI0580) |
| rseB | sigma-E factor regulatory protein (HI0630) |
| sigma factor regulatory protein, putative (HI0589) | |
| slyX | slyX protein (HI0573) |
| speF | ornithine decarboxylase (HI0591) |
| sun | sun protein (HI0624) |
| tagI | DNA-3-methyladenine glycosidase I (HI0654) |
| tex | transcription accessory protein (HI0568) |
| tfoX | DNA transformation protein (HI0601) |
| trkA | TRK system potassium uptake protein (HI0625) |
| trpS | tryptophanyl-tRNA synthetase (HI0637) |
| tufA | elongation factor Tu (HI0578) |
| tutB | elongation factor Tu (HI9632) |
| yecK | cytochrome C-type protein (HI0644) |

Acronyms of the genes comprising the 30,000 bp flanks of the ribosomal RNA operons of the genomically sequenced *H. influenzae* strain Rd.
rrnc flanks

| | |
|---|---|
| ansB | L-asparaginase II (HI0745) |
| clpP | ATP-dependent Clp protease, proteolytic subunit (HI0714) |
| clpX | ATP-dependent Clp protease, ATP-binding subunit (HI0715) |
| cyaY | cyaY protein (HI0727.5) |
| dapF | diaminopimelate epimerase (HI0750) |
| dcuB | anaerobic C4-dicarboxylate membrane transporter protein (HI0746) |
| dnaE | DNA polymerase III, alpha subunit (HI0739) |
| glpF | glycerol uptake facilitator protein (HI0690) |
| glpK | glycerol kinase (HI0691) |
| glpQ | glycerophosphoryl diester phosphodiesterase (HI0689) |
| glpT | glycerol-3-phosphatase transporter (HI0686) |
| gptB | xanthine-guanine phosphoribosyltransferase (HI0692) |
| hel | lipoprotein E (HI0693) |
| hemoglobin-binding protein (HI0712) | |
| htpX | heat shock protein (HI0720) |
| ilvD | dihydroxyacid dehydratase (HI0738.1) |
| lexA | lexA repressor (HI0749) |
| lipoprotein (HI0706) | |
| lppB | lipoprotein B (HI0703) |
| lysA | diaminopimelate decarboxylase (HI0727) |
| mutS | DNA mismatch repair protein (HI0707) |
| narP | nitrate/nitrite response regulator protein (HI0726) |
| ndh | NADH dehydrogenase (HI0747) |
| nusG | transcription antitermination protein (HI0717) |
| plsB | glycerol-3-phosphate acyltransferase (HI0748) |
| plsC | 1-acyl-glycerol-3-phosphate acyltransperase (HI0734) |
| proS | prolyl-tRNA synthetase (HI0729) |
| purL | phosphoribosylformylglycinamidine synthase (HI0752) |
| recQ | ATP-dependent DNA helicase (HI0728) |
| secB | protein-export protein (HI0742) |
| secE | preprotein translocase SecE subunit (HI0716) |
| selA | L-seryl-tRNA selenium transferase (HI0708) |
| selB | selenocysteine-specific elongation factor (HI0709) |
| slyD | peptidyl-prolyl cis-trans isomerase, FkbP-type (HI0699) |
| sufI | sufI protein (HI0733) |

Acronyms of the genes comprising the 30,000 bp flanks of the ribosomal RNA operons of the genomically sequenced *H. influenzae* strain Rd.
rrnc flanks

| | |
|---|---|
| surE | stationary-phase survival protein (HI0702) |
| tig | trigger factor (HI0713) |
| tpx | thiol peroxidase (HI0751) |
| trkH | TRK system potassium uptake protein (HI0723) |
| vacJ | lipoprotein (HI0718) |
| yhxB | phosphomannomutase (HI0740) |

Acronyms of the genes comprising the 30,000 bp flanks of the ribosomal RNA operons of the genomically sequenced *H. influenzae* strain Rd.
rrnD flanks

| | |
|---|---|
| ABC transporter, ATP-binding protein (HI0036) | |
| argG | argininosuccinate synthetase (HI1727) |
| betT | high-affinity choline transport protein (HI1706) |
| ccr | PTS system, glucose-specific IIA component (HI1711) |
| citC | citrate lyase ligase (HI0025) |
| citD | citrate lyase, gamma chain (HI0024) |
| citE | citrate lyase, beta chain (HI0023) |
| citF | citrate lyase, alpha chain (HI0022) |
| citG | citG protein (HI0021) |
| coA ligase long chain fatty acid coA ligase, putative (HI0002) | |
| dacA | penicillin-binding protein 5 (HI0029) |
| eda | 4-hydroxy-2-oxoglutarate aldolase/2-deydro-3-deoxyphosphogluconate aldolase (HI0047) |
| era | GTP-binding protein (HI0013) |
| fabI | enoyl-(acyl-carrier-protein) reductase (HI1734) |
| fdhD | fdhD protein (HI0005) |
| fdhE | fdhE protein (HI0009) |
| fdxH | formate dehydrogenase, beta subunit (HI0007) |
| fdxI | formate dehydrogenase, beta subunit (HI0008) |
| gapdH | glyceraldehyde-3-phosphate dehydrogenase (HI0001) |
| glnD | uridylyl transferase (HI1719) |
| gmk | guanylate kinase (HI1743) |
| holD | DNA polymerase III, psi subunit (HI0011) |
| mreB | rod shape-determining protein (HI0037) |
| mreC | rod shape-determining protein (HI0038) |
| mreD | rod shape-determining protein (HI0039) |
| lctD | L-lactate dehydrogenase (HI1739.1) |
| lepA | GTP-binding membrane protein (HI0016) |
| lepB | signal peptidase I(HI0015) |
| lipA | lipoate biosynthesis protein A (HI0026) |
| lipB | lipoate biosynthesis protein B (HI0027) |
| lipopolysaccharide biosynthesis protein, putative (HI1696) | |
| lipopolysaccharide biosynthesis protein, putative (HI1697) | |
| lipopolysaccharide biosynthesis protein (HI1698) | |
| lipopolysaccharide biosynthesis protein, putative (HI1699) | |
| lipopolysaccharide biosynthesis protein, putative (HI1700) | |
| map | methionine aminopeptidase (HI1722) |
| metE | 5-methyltetrahydropteroyltriglutamate-homocysteine methyltransferase (HI1702) |
| metR | transcriptional activator (HI1739) |
| murI | glutamate racemase (HI1739.2) |
| oxidoreductase (HI0048) | |
| pbp2 | penicillin-binding protein 2 (HI0032) |
| pepA | aminopeptidase A/I (HI1705) |
| phnA | alkylphosphonate uptake protein (HI0046) |
| ponB | penicillin-binding protein 1B (HI1725) |
| prfC | peptide chain release factor 3 (HI1735) |
| ptsH | phosphocarrier protein HPr (HI1713) |
| ptsI | phosphoenolpyruvate-protein phosphotransferase (HI1712) |
| purC | phosphoribosylaminoimidazole-succinocarboxamide synthase (HI1726) |
| recG | ATP-dependent DNA helicase (HI1740) |
| rfe | undecaprenyl-phosphate alpha-N-acetylglucosaminyltransferase (HI1716) |
| rimI | ribosomal-protein-alanine acetyltransferase (HI0010) |
| rnb | exoribonuclease II (HI1733) |

Acronyms of the genes comprising the 30,000 bp flanks of the
ribosomal RNA operons of the genomically sequenced
*H. influenzae* strain Rd.
rrnD flanks

| | |
|---|---|
| rnc | ribonuclease III (HI0014) |
| rodA | rod shape-determining protein (HI0031) |
| rpoZ | DNA-directed RNA polymerase, omega chain (HI1742) |
| spoT | guanosine-3',5'-bis(diphosphate) 3'-pyrophosphohydrolase (HI1741) |
| | transposase, putative (HI1721) |
| ung | uracil DNA glycosylase (HI0018) |
| xthA | exodeoxyribonuclease III (HI0041) |
| ygiX | transcriptional regulatory protein (HI1708) |
| ygiY | sensor protein (HI1707) |

Acronyms of the genes comprising the 30,000 bp flanks of the
ribosomal RNA operons of the genomically sequenced
*H. influenzae* strain Rd.
rrnE flanks

| | |
|---|---|
| acpP | acyl carrier protein (HI0154) |
| afuA | afuA protein (HI0131) |
| afuC | ferric ABC transporter, ATP-binding protein (HI0126) |
| bphH | glutathione transferase (HI0111) |
| conserved hypothetical transmembrane protein (HI0135) | |
| conserved hypothetical transmembrane protein (HI0147) | |
| cysS | cysteinyl-tRNA synthetase (HI0078) |
| dapE | succinyl-diaminopimelate desuccinylase (HI0102) |
| dcd | deoxycytidine triphosphate deaminase (HI0133) |
| dnaQ | DNA polymerase III, epsilon subunit (HI0137) |
| fabD | malonyl CoA-acyl carrier protein transacylase (HI0156) |
| fabG | 3-ketoacyl-acyl carrier protein reductase (HI0155) |
| fabH | beta-ketoacyl-ACP synthase III (HI0157) |
| ffh | signal recognition particle protein (HI0106) |
| glucose kinase, putative (HI0144) | |
| grpE | heat shock protein (HI0071) |
| GTP-binding protein (HI0136) | |
| hemR | hemin receptor (HI0113) |
| hflC | hflC protein (HI0150) |
| hflK | hflK protein (HI0151) |
| hitA | iron (III)ABC transporter, periplasmic-binding protein (HI0097) |
| hitB | iron (III)ABC transporter, permease protein (HI0098) |
| hitC | iron (III)ABC transporter, ATP-binding protein (HI0099) |
| htpG | heatshock protein (HI0104) |
| ldhA | D-lactate dehydrogenase, fermentative (HI0085) |
| metB | cystathionine gamma-synthase (HI0086) |
| metC | cystathionine beta-lyase H10122) |
| nagA | N-acetylglucosamine-6-phosphate deacetylase (HI0140) |
| nagB | glucosamine-6-phosphate isomerase (HI0141) |
| nanA | N-acetylneuraminate lyase (HI0142) |
| nrdD | anaerobic ribonucleoside-triphosphate reductase (HI0075) |
| ompP2 | outer membrane protein P2 (HI0139) |
| pgsA | phosphatidylglycerophosphate synthase (HI0123) |
| ppa | inorganic pyrophosphatase (HI0124) |
| ppiB | peptidyl-prolyl cis-trans isomerase B (HI0079) |
| recN | DNA repair protein (HI0070) |
| rnh | ribonuclease H (HI0138) |
| serS | seryl-tRNA transferase (HI0110) |
| tesB | acyl-CoA thioesterase II (HI0076) |
| thrA | aspartokinase I / homoserine dehydrogenase I (HI0089) |
| thrB | homoserine kinase (HI0088) |
| thrC | threonine synthase (HI0087) |
| trxM | thioredoxin (HI0084) |
| udk | uridine kinase (HI0132) |

Acronyms of the genes comprising the 30,000 bp flanks of the
ribosomal RNA operons of the genomically sequenced
*H. influenzae* strain Rd.
rrnF flanks

| | |
|---|---|
| adhC | alcohol dehydrogenase, class III (HI0185) |
| aefA | conserved hypothetical transmembrane protein (HI0195) |
| | amino acid carrier protein, putative (HI0183) |
| aroB | 3-dehydroquinate synthase (HI0208) |
| aroC | chorismate synthase (HI0196) |
| aroK | shikimic acid kinase I (HI0207) |
| | arsenate reductase, putative (HI0236) |
| bcp | bacterioferritin comigratory protein (HI0254) |
| birA | biotin operon repressor/biotin acetyl coenzyme A carboxylase synthetase (HI0220) |
| brnQ | branched chain amino acid transport system II carrier protein (HI0226) |
| | esterase (HI0184) |
| | esterase/lipase, putative (HI0192) |
| dam | DNA adenine methylase (HI0209) |
| dapA | dihydrodipicolinate synthetase (HI0255) |
| deaD | ATP-dependent RNA helicase (HI0231) |
| exbB | biopolymer transport protein (HI0253) |
| exbD | biopolymer transport protein (HI0252) |
| fldA | flavodoxin (HI0191) |
| fur | ferric uptake regulation protein (HI0190) |
| gdhA | glutamate dehydrogenase (HI0189) |
| | glycosyl transferase, putative (HI0258) |
| guaA | GMP synthase (HI0222) |
| guaB | inosine-5'-monophosphate dehydrogenase (HI0221) |
| hsdS | type I restriction/modification specificity protein (HI0216) |
| hxuB | heme-hemopexin utilization protein B (HI0263) |
| hxuA | heme-hemopexin utilization protein A (HI0264) |
| menE | O-succinylbenzoate--CoA ligase (HI0194) |
| mepA | penicillin-insensitive murein endopeptidase (HI0197) |
| msbB | lipid A biosynthesis (kdo)2-(lauroyl)-lipid IVA acyltransferase (HI0199) |
| murB | UDP-N-acetylenolpyruvoylglucosamine reductase (HI0268) |
| narQ | nitrate/nitrite-sensor protein (HI0267) |
| nhaA | Na+/H+ antiporter (HI0225) |
| | oligopeptide transporter, periplasmic-binding protein, putative (HI0213) |
| pfl | formate acetyltransferase (HI0180) |
| | formate transporter (HI0181) |
| pgpB | phosphatidylglycerophosphatase B (HI0211) |
| pnp | polynucleotide phosphorylase (HI0229) |
| prlC | oligopeptidase A (HI0214) |
| queA | queuosine biosynthesis protein (HI0245) |
| rarD | rarD protein, putative (HI0223) |
| ribA | GTP cyclohydrolase II (HI0212) |
| rpL19 | ribosomal protein L19 (HI0201) |
| rpS16 | ribosomal protein S16 (HI0204) |
| secD | protein-export membrane protein (HI0240) |
| secF | protein-export membrane protein (HI0239) |
| selD | selenide, water dikinase (HI0200) |
| seqA | seqA protein (HI0193) |
| sigma(54) | sigma(54) modulation protein, putative (HI0257) |
| ssb | single-stranded DNA binding protein (HI0250) |
| | sugar kinase, putative (HI0182) |
| tgt | tRNA-guanine transglycosylase (HI0244) |
| | transcriptional regulator, putative (HI0186) |
| tonB | tonB protein (HI0251) |
| trmD | tRNA (guanine-N1)-methyltransferase (HI0202) |
| uvrA | excinuclease ABC, subunit A (HI0249) |
| | 5'-nucleotidase, putative (HI0206) |

Genes flanking rrnA in *Escherichia coli* MG1655

| gene acronym | function |
|---|---|
| 5' flanking region of rrnA (5' → 3'): | |
| pldA | detergent-resistant phospholipase A |
| recQ | DNA-dependent ATPase, DNA helicase |
| yigJ | hypothetical 13.3 kD protein in recQ 3' region |
| yigK | hypothetical 15.4 kD protein in recQ-pldB intergenic region |
| pldB | lysophospholipase L2 |
| yigL | o171; This 171 aa ORF is 99 pct identical to 171 residues of a 208 aa protein YIGL_ECOLI SW: P27848 but contains −37 additional N-ter aa residues |
| yigM | hypothetical 33.7 kD protein in pldB-metR intergenic region |
| metR | trans-activator of metE and metH |
| metE | 5-methyltetrahydropteroyltriglutamate- homocysteine methyltransferase |
| Unnamed | f332; revealed by sequence change relative to earlier version; similar to Methylobacterium extorquens orf2, GB: U72662 |
| upd | uridine phosphorylase |
| yigN | hypothetical 54.7 kD protein in udp 3' region precursor (o475) |
| yigO | hypothetical 28.1 kD protein in udp-rfaH intergenic region |
| yigP | hypothetical 22.3 kD protein in udp-rfaH intergenic region |
| Unnamed | hypothetical 63.2 kD protein in udp-rfaH intergenic region |
| Unnamed | hypothetical 11.3 kD protein in udp-rfaH intergenic region |
| Unnamed | hypothetical 12.1 kD protein in udp-rfaH intergenic region |
| Unnamed | hypothetical 15.6 kD protein in udp-rfaH intergenic region |
| yigU | o258; sequence change joins two ORFs relative to earlier version; 97.7 pct identical to the conceptual ORF YIGU_ECOLI SW: P27857 |
| yigW | o206; 98 pct identical to N-terminal 184 residues of 264 aa conceptual translation YIGW_ECOLI SW: P27859 |
| yigW | o113; 100 pct identical to 80 residues of a 264 aa conceptual translation YIGW_ECOLI SW: P27859 but has −151 additional N-terminal residues |
| rfaH | transcriptional activator rfaH |
| yigC | o497; ? ? ? pct identical to conceptual translation YIGC_ECOLI SW: P26615 |
| ubiB | flavin reductase |
| fadA | small (beta) subunit of the fatty acid-oxidizing multienzyme complex |
| fadB | large (alpha) subunit of the fatty acid-oxidizing multienzyme complex |
| pepQ | proline dipeptidase |
| yigZ | hypothetical 21.9 kD protein in pepQ-trkH intergenic region |
| trkH | o432; This 431 aa ORF is 100 pct identical to 416 residues of an approx. 488 aa protein TRKH_ECOLI SW: P21166 |
| Unnamed | o181 |
| 3' flanking region of rrnA (5' → 3'): | |
| Unnamed | f170; matches PS00017: ATP_GTP_A |
| mobA | motybdoptenrin-guanine dinucleotide biosynthesis protein A |
| yihD | hypothetical 10.3 kD protein in mobA 3' region (o89) |
| yihE | hypothetical 38.1 kD protein in dsba 5' region (o328) |
| dsbA | o208; 100 pct identical amino acid sequence and equal length-to DSBA_ECOLI SW: P24991 |
| yihF | hypothetical 54.1 kD protein in dsbA 3' region (o490) |
| yihG | hypothetical 36.3 kD protein in polA 5' region (f310) |
| polA | DNA polymerase I |
| Unnamed | f199; matches PS00017: ATP_GTP_A |
| yihI | hypothetical 19.1 kD protein in polA-hemN intergenic region |
| hemN | oxygen-independent coproporphyrinogen III oxidase |
| glnG | f469; 100 pct identical to NTRC_ECOLI SW: P06713; CG Site No. 702 |
| glnL | f349; 100 pct identical to NTRB_ECOLI SW: P06712; CG Site No. 701 |
| glnA | glutamine synthetase |
| yihK | 65.4 kD GTP-binding protein in glnA-fdhE intergenic region |
| Unnamed | o236; close match to PS00043: HTH_GNTR_FAMILY; similar to *E. coli* hypoth. 30 kDa protein adjacent to suc operon |
| yihM | hypothetical 36.9 kD protein in glna-fdhe intergenic region |
| yihN | hypothetical 46.3 kD protein in glna-fdhe intergenic region |
| Unnamed | f230; sequence change split yihO (YIHO_ECOLI SW: P32136) |
| Unnamed | f487; sequence change split yihO (YIHO_ECOLI SW: P32136) |
| yihP | hypothetical 51.7 kD protein in glnA-fdhE intergenic region |
| yihQ | hypothetical 77.2 kD protein in glnA-fdhE intergenic region |
| yihR | hypothetical 34 kD protein in glna-fdhe intergenic region (f3 |
| yihS | hypothetical 48 kD protein in glna-fdhe intergenic region (f4 |

| _____ |
|---|
| Genes flanking rrnB-rrnE in *Escherichia coli* MG1555 |

| gene acronym | function |
|---|---|
| 5' flanking region of rrnB (5' → 3'): | |
| yijE | hypothetical 34.1 kD protein in katg-gida intergenic region |
| yijF | hypothetical 23.0 kD protein in katg-gida intergenic region |
| gldA | glycerol dehydrogenase |
| talC | transaldolase-like protein |
| ptsA | phosphoenolpyruvate-protein phosphotransferase ptsa |
| yijI | hypothetical 11.8 kD protein in ptsa-frwc intergenic region |
| frwC | pts system, fructose-like-2 IIc component (phosphotransferase |
| frwB | pts system, fructose-like-2 IIb component 1 (phosphotransfera |
| pflD | formate acetyltransferase 2 (pyruvate formate-II |
| pflC | probable pyruvate formate-lyase 2 activating enzyme |
| frwD | PTS system, fructose-like-2 IIB component 2 (phosphotransferase) |
| yijO | hypothetical transcriptional regulator in glda- ppc intergenic |
| yijP | hypothetical 66.6 kD protein in frwd-ppc intergenic region |
| ppc | phosphoenolpyruvate carboxylase |
| argE | acetylornithine deacetylase |
| argC | N-acetyl-gamma-glutamyl-phosphate reductase |
| argB | acetylglutamate kinase |
| argH | argininosuccinate lyase |
| oxyR | hydrogen peroxide-inducible genes activator |
| udhA | unknown dehydrogenase a |
| yijC | hypothetical 26.6 kD protein in udha-trma intergenic region |
| yijD | o119 |
| trmA | tRNA (uracil-5)-methyltransferase |
| btuB | vitamin b12 receptor precursor |
| murI | glutamate racemase |
| 3' flanking region of rrnB and 5' flanking region of rrnE (5' → 3'): | |
| murB | UDP-N-acetylenolpyruvoylglucosamine reductase |
| birA | bifunctional protein: biotin operon repressor and biotin-[acetyl-CoA carboxylase] synthetase |
| coaA | pantothenate kinase |
| Unnamed | f51; This 51 aa ORF is 33 pct identical (1 gap) to 33 residues of an approx 176 aa protein OBP_RAT SW: P08937 |
| tufB | elongation factor EF-Tu (dupilcate gene) |
| secE | preprotein transiocase sece subunit |
| nusG | transcription antitermination protein nusg |
| rplK | 50S ribosomal subunit protein L11 |
| rplA | 50S ribosomal subunit protein L1 |
| rplJ | 50S ribosomal subunit protein L10 |
| rplL | 50S ribosomal subunit protein L7/L12 |
| rpoB | DNA-directed RNA polymerase beta-subunit |
| rpoC | DNA-directed RNA polymerase, beta'-subunit |
| htrC | heatshock protein C |
| thiH | thih protein |
| thiG | f281; This 281 aa ORF is 99 pct identical to 281 residues of a 324 aa protein THIG_ECOLI SW: P30139 but contains -43 additional N-ter aa and about 0 C-ter residues |
| thiF | f245; This 245 aa ORF is 100 pct identical to 245 residues of a 251 aa protein THIF_ECOLI SW: P30138 but contains -6 additional N-ter aa and about 0 C-ter residues |
| thiE | thie protein |
| thiC | thic protein |
| Unnamed | f158; similar to Pseudomonas aeruginosa alginate regulatory protein AlgR2 |
| yjaD | hypothetical 29.8 kD protein in thic-heme intergenic region |
| hemE | uroporphyrinogen decarboxylase |
| yjaF | hypothetical 24.9 kD protein in heme-hupa intergenic region |
| yjaG | hypothetical 22.6 kD protein in hem-hupa intergenic region |
| hupA | histonelike DNA-binding protein HU-alpha (NS2) (HU-2) |
| yjaH | hypothetical 26.3 kD protein in hupa-hydh intergenic region |
| yjaI | hypothetical 20.4 kD protein in hupa-hydh intergenic region |
| hydH | o465 |
| hydG | transcriptional regulatory protein hydg |
| purD | phosphoribosylglycineamide synthetase |
| purH | phosphoribosylaminoimidazolecarboxamide formyltransferase and IMP cyclohydrolase (bifunctional enzyme) |
| 3' flanking region of rrnE (5' → 3'): | |
| yjaA | hypothetical 14.4 kD protein in rrfE-metB intergenic region |
| yjaB | hypothetical 16.4 kD protein in rrfE-metA intergenic region |
| metA | homoserine O-succinyltransferase |
| aceB | malate synthase A |
| aceA | isocitrate lyase |
| aceK | isocitrate dehydrogenase kinase/phosphatase |

Genes flanking rrnB-rrnE in *Escherichia coli* MG1555

| gene acronym | function |
| --- | --- |
| arp | hypothetical 82.6 kD protein in acek-iclR intergenic region |
| iclR | acetate operon repressor |
| metH | B12-dependent homocysteine-N5-methyltetrahydrofolate transmethylase |
| yjbB | hypothetical 59.5 kD protein in meth-pepe intergenic region |
| pepE | peptidase E |
| yjbC | hypothetical 32.5 kD protein in pepe-lysc intergenic region |
| yjbD | hypothetical 10.5 kD protein in pepe-lysc intergenic region |
| lysC | lysine-sensitive aspartokinase III |
| pgi | glucose-6-phosphate isomerase |
| yjbE | hypothetical 7.4 kD protein in pgi-xyle intergenic region |
| yjbF | hypothetical 25.0 kD lipoprotein in pgi-xylE intergenic region |
| yjbG | hypothetical 26.3 kD protein in pgi-xylE intergenic region |
| yjbH | hypothetical 78.5 kD protein in pgi-xylE intergenic region |
| yjbA | o136 |
| xylE | xylose-proton symport |
| malG | maltose transport inner membrane protein |
| malF | maltose transport inner membrane protein |
| malE | periplasmic maltose-binding protein |

Genes flanking rrnC in *Escherichia coli* MG1655

| gene acronym | function |
| --- | --- |
| 5' flanking region of rrnC (5' → 3'): | |
| pstS | periplasmic phosphate-binding protein |
| glmS | glutamine amidotransferase; glucosamine- fructose-6-phosphate aminotransferase |
| glmU | ??? |
| atpC | ATP synthase F1 epsilon subunit |
| atpD | ATP synthase F1 beta subunit |
| atpG | ATP synthase F1 gamma subunit |
| atpA | ATP synthase F1 alpha subunit |
| atpH | ATP synthase F1 delta subunit |
| atpF | ATP synthase F0 subunit b |
| atpE | ATP synthase F0 subunit c; DCCD-binding protein |
| atpB | ATP synthase F0 subunit a |
| atpI | ATP synthase subunit? |
| gidB | glucose inhibited division protein |
| gidA | glucose inhibited division protein |
| mioC | MioC protein; involved in modulation of initiation at oriC |
| asnC | regulatory protein |
| asnA | asparagine synthetase A |
| Unnamed | hypothetical 49.6 kD protein in asnA 3' region |
| yieN | hypothetical 57.4 kD protein in asnA-kup intergenic region |
| kup | o519; 100 pct identical (0 gaps) to 505 residues of the 624 aa protein KUP_ECOLI SW: P30016 |
| rbsD | high affinity ribose transport protein RbsD |
| rbsA | high affinity ribose transport protein |
| rbsC | high affinity ribose transport protein |
| rbsB | periplasmic ribose-binding protein precursor |
| rbsK | ribokinase |
| rbsR | rbs repressor |
| yieO | hypothetical 51.5 kD protein in rbsR-rrsC intergenic region |
| yieP | hypothetical 20.8 kD protein in rbsR-rrsC intergenic region |
| 3' flanking region of rrnC (5' → 3'): | |
| yifA | hypothetical 22.4 kD protein in trpT-pssR intergenic region |
| yifE | hypothetical 13.1 kD protein in pssR-ilvL intergenic region |
| yifB | hypothetical 56.2 kD protein in pssR-ilvL intergenic region |
| ilvL | ilvGMEDA operon leader peptide |
| ilvG | acetohydroxy acid synthase II, large subunit |
| ilvM | acetohydroxy acid synthase II, small subunit |
| ilvE | branched-chain amino-acid aminotransferase |
| ilvD | dihydroxyacid dehydratase |
| itvk | threonine deaminase; threonine dehydratase biosynthetic |
| ilvY | f297; 100 pct identical amino acid sequence and equate length to tlVY_ECOLI SW: P05827 |
| ilvC | ketol-acid reductoisomerase |
| ppiC | peptidyl-protyl cis-trans isomerase C |

Genes flanking rrnC in *Escherichia coli* MG1655

| gene acronym | function |
|---|---|
| Unnamed | residues 13–91 are 43 pct identical to aa 64–142 from hypothetical protein Y080_HAEIN SW; P43936 (143 aa) |
| Unnamed | residues 21–80 are 51 pct identical (2 gaps) to aa 8–59 from hypothetical protein Y080_HAEIN SW; P43936 (143 aa) |
| rep | ATP-dependent DNA helicase Rep |
| gppA | guanosine-5'-triphosphate, 3'-diphosphate pyrophosphatase (guanosine pentaphosphatase) |
| rhlB | 99 pct identical amino acid sequence and equal length to RHLB_ECOLI SW: P24229; member of DEAD helicase family; probably rnmr |
| trxA | thioredoxin |
| rhoL | rho operon leader peptide |
| rho | transcription termination factor rho |
| rfe | putative undecaprenyl-phosphate alpha-n- acetylglucosaminyltra |
| Unnamed | o349 |
| rffE | o389; This 389 aa ORF is 99 pct identical (1 gap) to 375 residues of an approx. 384 aa protein NFRC ECOLI SW: P27828 |

Genes flanking rrnD in *Escherichia coli* MG1655

| gene acronym | function |
|---|---|
| 5' flanking region of rrnD (5' → 3'): | |
| Unnamed | hypothetical 107.7 kD protein in argR-cafA intergenic region |
| yhdR | hypothetical 31.5 kD protein in argR-cafA intergenic region |
| cafA | cytoplasmic axial filament protein |
| yhdE | hypothetical 21.5 kD protein in cafA-mreD- intergenic region |
| mreD | rod shape-determining protein MreD |
| mreC | rod shape-determining protein MreC |
| mreB | rod shape-determining protein mreb |
| yhdA | hypothetical 73.3 kD protein in mreB-accB intergenic region |
| yhdH | o324 |
| Unnamed | f33; This 33-aa ORF is 57 pct identical (1 gap) to 21 residues of an approx. 304 aa protein NC5R_HUMAN SW: P00387 |
| accB | biotin carboxyl carrier protein |
| accC | biotin carboxylase |
| yhdT | hypothetical 9.1 kD protein in accC-panF intergenic region |
| panF | pantothenate permease |
| prmA | ribosomal protein L11 methyltransferase |
| yhdG | hypothetical 35.9 kD protein in pmrA-fis intergenic region |
| fis | o98; CG Site No. 18328 |
| yhdJ | hypothetical adenine-specific methylase in fis- envR intergenic region |
| Unnamed | o59 |
| envR | potential acref/envcd operon repressor |
| acrE | o385; alternate name envC; 100 pct identical amino acid sequence and equal length to ACRE_ECOLI SW: P24180 |
| acrF | o1034; alternate name envD, has different start annotated; 99 pct identical amino acid sequence and equal length to ACRF_ECOLI SW: P24181 |
| yhdV | hypothetical 7.5 kD protein in acrF-rrnD intergenic region |
| yhdW | hypothetical amino acid ABC transporter in acrF- rrnD intergenic region |
| yhdX | hypothetical 40.4 kD protein in acrF-rrnD intergenic region |
| yhdY | hypothetical 41.6 kD protein in acrF-rrnD intergenic region |
| yhdZ | hypothetical ABC transporter in acrF-rrnD intergenic region |
| 3' flanking region of rrnD (5' → 3'): | |
| Unnamed | o256 |
| yrdB | hypothetical 10.0 kD protein in rrnd-aroe intergenic region |
| aroE | shikimate dehydrogenase |
| yrdC | hypothetical protein in aroE-smg intergenic region |
| yrdD | hypothetical 18.6 kD protein in aroE-smg intergenic region |
| smg | hypothetical 18.6 kD protein in aroE-smg intergenic region |
| smf | f102; 99 pct identical to 102 residues of 374 aa SMF_ECOLI SW: P30852 but has 272 additional N-terminal residues; frameshift difference from GB: ECSMFSMG; X65946 |
| smf | f253; 100 pct identical to N-terminal 248 residues of 374 aa SMF_ECOLI SW: P30852; frameshift difference from GB: ECSMFSMG; X65946 |
| def | N-formylmethionylaminoacyl-tRNA deformylase |
| fmt | methionyl-tRNA formyltransferase |

Genes flanking rrnD in Escherichia coli MG1655

| gene acronym | function |
| --- | --- |
| fmu | 0429; we have one ORF, ECFMT has fmu and fmv; this 429 aa ORF is 100 pct identical to FMU_ECOLI SW: P36929 |
| trkA | TrkA protein of the constitutive K+ transport system Trk |
| mscL | o136; 100 pct identical amino acid sequence and equal length to MSCL_ECOLI SW: P23867 |
| ydhM | hypothetical transcriptional regulator in mscL- rplQ intergenic region |
| yhdN | hypothetical 13.9 kD protein in mscL-rplQ intergenic region |
| rplQ | 50S ribosomal subunit protein L17 |
| rpoA | f329; CG Site No. 234; 100 pct identical amino acid sequence and equal Length to RPOA_ECOLI SW: P00574 |
| rpsD | 30S ribosomal subunit protein S4 |
| rpsk | 30S ribosomal subunit protein S11 |
| rpsM | 30S ribosomal subunit protein S13 |
| rpmJ | 50S ribosomal subunit protein L36 |
| prlA | preprotein translocase secy subunit |
| rplO | 50S ribosomal subunit protein L15 |
| rpmD | 50S ribosomal subunit protein L30 |
| rpsE | 30S ribosomal subunit protein S5 |
| rplR | 50S ribosomal subunit protein L18 |
| rplF | 50S ribosomal subunit protein L6 |
| rpsH | 30S ribosomal subunit protein S8 |
| rpsN | 30S ribosomal subunit protein S14 |
| rplX | 50S ribosomal subunit protein L5 |
| rplX | 50S ribosomal subunit protein L24 |
| rplN | 50S ribosomal subunit protein L14 |
| rpsQ | 30S ribosomal subunit protein S17 |
| rpmC | 50S ribosomal subunit protein L29 |
| rplP | 50S ribosomal subunit protein L16 |
| rpsC | 30S ribosomal subunit protein S3 |
| rpiV | 50S ribosomal subunit protein L22 |
| rpsS | 30S ribosomal subunit protein S19 |
| rplB | 50S ribosomal subunit protein L2 |
| rplW | 50S ribosomal subunit protein L23 |
| rpiD | 50S ribosomal subunit protein L4 |
| rplC | 50S ribosomal subunit protein L3 |
| rpsJ | 30S ribosomal subunit protein S10 |
| pinO | pino rotein |

Genes flanking rrnG in Escherichia coli MG1655

| gene acronym | function |
| --- | --- |

5' flanking region of rrnG (5' → 3'):

| | |
| --- | --- |
| yfhD | hypothetical 53.2 kD protein in purL-dpj intergenic region |
| yfhC | hypothetical 20.0 kD protein in purL-dpj intergenic region |
| yfhB | hypothetical 21.9 kD protein in purL-dpj intergenic region |
| yfhH | hypothetical protein in purL-dpj intergenic region |
| Unnamed | o86; This 86 aa ORF is 59 pct identical (1 gap) to 76 residues of an approx. 88 aa protein FER_CHRVI SW: P00208 |
| acpS | Dpj protein |
| pdxJ | pyridoxal phosphate biosynthetic protein PdxJ |
| recO | DNA repair protein RecO |
| era | GTP-binding protein |
| rnc | ribonuclease III |
| lepB | signal peptidase I |
| lepA | GTP-binding protein LepA |
| rseC | sigma-E factor regulatory protein RseC |
| rseB | sigma-E factor regulatory protein RseB precursor |
| rseA | sigma-E factor negative regulatory protein |
| rpoE | RNA polymerase sigma-E factor (sigma-24) |
| nadB | I-aspartate oxidase (quinolinate synthetase B). |
| yfiC | hypothetical protein in nadB-srmB intergenic region |
| srmB | ATP-dependent RNA helicase SrmB |
| yfiE | hypothetical protein in the srmB-ung intergenic region |
| yfiK | hypothetical 21.2 kD protein in srmB-ung intergenic region |
| yfiD | hypothetical 14.3 kD protein in srmB-ung intergenic region |
| ung | uracil-DNA glycosylase |
| yfiF | hypothetical 37.8 kD protein in ung 3' region |
| yfiG | hypothetical protein in the ung 3' region |

Genes flanking rrnG in *Escherichia coli* MG1655

| gene acronym | function |
|---|---|
| Unnamed | o240; This 240 aa ORF is 32 pct identical (2 gaps) to 62 residues of an approx. 2560 aa protein 7LES_DROME SW; P13368 |
| Unnamed | o856; This 886 aa ORF is 25 pct identical (10 gaps) to 150 residues of an approx. 336 aa protein SUCA_RAT SW: P13086 |
| pssA | CDP-diacylglycerol-serine O- phosphatidyltransferase |
| yfiM | hypothetical 9.9 kD protein in pss-kgtP intergenic region |
| kgtP | alpha-ketoglutarate permease |

3' flanking region of rrnG (5' → 3'):

| | |
|---|---|
| cipB | ClpB protein (heat shock protein f84.1) |
| yfiH | hypothetical 26.3 kD protein in clpB 5' region |
| sfhB | ftsH suppressor protein SfhB |
| Unnamed | o245; 42 pct identical to Y177_HAEIN SW: P44553 (262 aa hypothetical protein HI0177) |
| Unnamed | o68; ttg start |
| yfiA | o113; 100 pct identical to YFIA_ECOLI SW: P11285 (12.7 kD protein in pheL 5' region; belongs to the sigma(54) modulation protein family |
| yfiA | o113; 100 pct identical to YFIA_ECOLI SW: P11285 (12.7 kD protein in pheL 5' region; belongs to the sigma(54) modulation protein family |
| pheA | chorismate mutase-P/prephenate dehydratase |
| tyrA | chorismate mutase/prephenate dehydrogenase |
| aroF | phospho-2-dehydro-3-deoxyheptonate aldolase, tyr-sensitive |
| yfiL | hypothetical protein in aroF-rplS intergenic region |
| Unnamed | o172; This 172 aa ORF is 28 pct identical (1 gap) to 59 residues of an approx. 2720 aa protein G156_PARPR SW:P13837 |
| yfiN | hypothetical protein in rplS 5' region |
| yfiB | hypothetical 17.2 kD protein in rplS 5' region |
| rplS | 50S ribosomal subunit protein L19 |
| trmD | tRNA(guanine-7)methyltransferase |
| yfjA | hypothetical 21.0 kD protein in trmD-rpsP intergenic region |
| rpsP | 30S ribosomal subunit protein S16 |
| ffh | signal recognition particle protein |
| Unnamed | o288; This 288 aa ORF is 26 pct identical (8 gaps) to 204 residues of an approx. 272 aa protein YNR3_AZOBR SW: P45674 |
| Unnamed | o196; uug start; This 196 aa ORF is 27 pct identical (15 gaps) to 185 residues of an approx. 440 aa protein YTFL_HAEIN SW: P44717 |
| yfjD | hypothetical protein in grpE 3' region |
| grpE | heat shock protein grpE (heat shock protein b25.3) (hsp24) |
| yfjB | o292; Residues 1–119 are 99 pct identical to N-ter of YFJB_ECOLI SW: P37768; residues 215–281 are 100 pct identical to C-ter of YFJE_ECOLI SW: P46140 |
| recN | 0553; 100 pct identical to GB: ECU36840_2 ACCESSION: U36840; CG Site No. 10872; alternate name radB; a frame-shift error in GB ACCESSION: Y00357 changes the C-terminal end of the gene |
| smpA | small protein A |
| Unnamed | f102; This 102 aa ORF is 55 pct identical (1 gap) to 94 residues of an approx. 104 aa protein Y395_HAEIN SW: P43994 |
| Unnamed | f158 |
| smpB | small protein B |
| intA | SlpA integrase; prophage CP4-57 integrase |
| Unnamed | f318; 31 pct identical (5 gaps) to 87 residues from HUS2_YEAST SW: P46957 (487 aa) |
| alpA | prophage cp4-57 regulatory protein AlpA |
| Unnamed | o469; This 469 aa ORF is 26 pct identical (2 gaps) to 73 residues of an approx. 392 aa protein DHE4_SULSH SW: P39475 |
| Unnamed | o469; This 469 aa ORF is 26 pct identical (2 gaps) to 73 residues of an approx. 392 aa protein DHE4_SULSH SW: P39475 |

Genes flanking rrnH in *Escherichia coli* MG1655

| gene acronym | function |
|---|---|

5' flanking region of rrnH (5' → 3'):

| | |
|---|---|
| frr | ribosome recycling factor |
| yaeM | hypothetical protein in frr 3' region |
| Unnamed | o253; 61 pct identical to 229 residues of an approx. 240 aa hypothetical protein- Y920_HAEIN SW: P44938 |
| cdsA | phosphatidate cytidylyltransferase |
| yaeL | hypothetical protein in cdsA 3' region |

-continued

Genes flanking rrnH in *Escherichia coli* MG1655

| gene acronym | function |
|---|---|
| Unnamed | o810; 45 pct identical (29 gaps) to 808 residues of an approx. 800 aa protein D151_HAEIN SW: P46024 |
| hlpA | histone-like protein Hlp-1 precursor |
| lpxD | USP-3-O-[3-hydroxymyristoyl]glucosamine N-acyltransferase |
| fabZ | (3R)-hydroxymyristol acyl carrier protein dehydrase |
| lpxA | acyl-[acyl-carrier-protein]: UDP-N-acetylglucosamine O-acyltransferase |
| lpxB | lipid-A-disaccharide-synthase |
| rnhB | ribonuclease HII |
| dnaE | DNA polymerase III, alpha chain |
| accA | acetyl-coenzyme A carboxylase carboxyl transferase subunit alpha |
| idcC | lysine decarboxylase |
| Unnamed | o138; 65 pct identical to 126 residues of an approx. 136 aa protein YWKD_BACSU SW: P45871 |
| mesJ | celt cycle protein MesJ |
| yaeO | hypothetical protein in acCA-cutF intergenic region |
| yaeQ | hypothetical protein in acCA-cutF intergenic region |
| yaeJ | hypothetical protein in acCA-cutF intergenic region |
| cutF | copper homeostasis protein cutF precursor (lipoprotein ntpE) |
| yaeF | hypothetical 32.1 kD lipoprotein in cutF-proS intergenic region |
| proS | protyl-tRNA synthetase |
| yaeB | hypothetical 26.4 kD protein in proS-rcsF intergenic region |
| rcsF | f134; 97 pct identical (1 gap) to RCSF_ECOLI SW: P28633 |
| yaeC | hypothetical 29.4 kD lipoprotein in rcsF-rrnH intergenic region |
| yaeE | f218; 100 pct identical to YAEE_ECOLI SW: P31547 |
| abc | f343; 98 pct identical to fragment (231 aa) ABC_ECOLI SW: P30750; 65 pct identical (1 gap) to 345 aa ABC_HAEIN SW: P44785 |
| yaeD | hypothetical 21.3 kD protein in abc-rrsH intergenic region |
| 3' flanking region of rrnH (5' → 3'): | |
| yafB | hypothetical 29.4 kD protein in aspU-dniR intergenic region |
| yafC | hypothetical transcriptional regulator in rrnH- dniR intergenic region |
| yafD | hypothetical protein in aspU-dniR intergenic region |
| yafE | hypothetical 23.0 kD protein in aspU-dniR intergenic region |
| dniR | regulatory protein DniR and hypothetical YafG |
| Unnamed | f251; 100 pct identical to GB: ECOTSF_31 ACCESSION: D83536; 46 pct identical (1 gap) to hypothetical protein YRNH_BUCAP SW: Q08889 |
| Unnamed | o246 |
| rnhA | ribonuclease H |
| dnaQ | DNA polymerase III epsilon subunit |
| Unnamed | o261 |
| Unnamed | f112 |
| Unnamed | f256; 100 pct identical to hypothetical protein GB: ECOTSF_35 ACCESSION: D83536 |
| Unnamed | o157 |
| Unnamed | f826; 99 pct identical to 814 aa hypothetical protein GB: ECOTSF_36 ACCESSION: D83536 but has 12 additional N-terminal residues; similar to P. mirabilis uroporphyrinogen III methylase GB: PMU22969_1 ACCESSION: U22969 |
| gmhA | phosphoheptose isomerase |
| yafJ | hypothetical protein in gmhA-fhiA intergenic region |
| yafK | hypothetical protein in gmhA-fhiA intergenic region |
| yafQ | hypothetical protein in gmhA-fhiA intergenic region |
| Unnamed | f86; 100 pct identical to GB: ECODINJ_6 ACCESSION: D38582 |
| yafL | hypothetical protein in gmhA-fhiA intergenic region |
| yafM | hypothetical protein in gmhA-fhiA intergenic region |
| fniA | hypothetical protein FhiA |
| mbhA | o211; Residues 2–211 are 100 pct identical to hypothetical protein MbhA GB: ECODINJ_10 ACCESSION: D38582; Residues 51-211 are 100 pct identical to residues 1–161 of 161 aa hypothetical protein GB: ECOTSF_38 ACCESSION: D83536 |
| dinP | hypothetical protein DinP |
| yafN | hypothetical protein in mbhA-prfH intergenic region |
| yafO | hypothetical protein in mbhA-prfH intergenic region |
| yafP | hypothetical protein in mbhA-prfH intergenic region |
| | o88 |
| prfH | peptide chain release factor homolog (RF-H) |
| pepD | aminoacyl-histidine dipeptidase precursor |

I claim:

1. A method for vaccine development, said method comprising carrying out, in the order given below, the steps of:

a) providing a plurality of isolates of a single bacterial species, said isolates comprising DNA;

b) examining said DNA from said isolates so as to produce a phylogenetic tree defining one or more phylogenetic subsets of said isolates, wherein said phylogenetic tree is produced prior to evaluation of a candidate vaccine target antigen and wherein construction of said tree is not based on examination of the DNA sequence of a gene encoding any candidate vaccine target antigen; and c) evaluating a candidate vaccine target antigen in a representative isolate from each of said one or more stubsets of isolates for variability.

2. A method for vaccine development, said method comprising the steps of:

a) providing one or more phylogenetic subsets of isolates, wherein said phylogenetic subsets of isolates are defined by a phylogenetic tree produced by a method comprising the steps of:

1) providing a plurality of isolates of a single bacterial species, said isolates comprising DNA; and 2) examining said DNA from said isolates so as to produce a phylogenetic tree defining one or more phylogenetic subsets of said isolates, wherein said phylogenetic tree is produced prior to evaluation of a candidate vaccine target antigen and wherein construction of said tree is not based on examination of the DNA sequence of a gene encoding any candidate vaccine target antigen; and b) evaluating a candidate vaccine target antigen in a representative isolate from each of said one or more subsets of isolates for variability.

3. The method of claim 1 or claim 2, wherein said evaluating step comprises examining the gene encoding said candidate vaccine target antigen for conserved nucleic acid sequences among said isolate subsets.

4. The method of claim 1 or claim 2, wherein said evaluating step comprises examining a gene encoding an essential enzyme in the biosynthesis of said candidate vaccine target antigen for conserved nucleic acid sequences among said isolate subsets.

5. The method of claim 1 or claim 2, wherein said candidate vaccine target antigen is a bacterial surface protein.

6. The method of claim 5, wherein said evaluating step comprises examining the primary amino acid sequence of said bacterial surface protein for conserved amino acid sequences among said isolate subsets.

7. The method of claim 6, further comprising the steps of identifying in said candidate vaccine target antigen an amino acid sequence that is conserved among said isolate subsets and synthesizing said amino acid sequence to produce a test peptide vaccine.

8. The method of claim 7, further comprising the step of immunizing an animal with said test peptide vaccine.

9. The method of claim 1 or claim 2, wherein said examining step comprises the steps of:

isolating bacterial DNA from each of said isolates under conditions such that a DNA preparation is produced for each isolate, said DNA preparation comprising DNA flanking the DNA encoding 16S and 23S rRNA;

digesting said DNA preparations with one or more restriction enzymes under conditions such that restriction fragments are produced, said restriction fragments comprising a digestion product for each of said isolates, each said digestion product comprising a portion of said DNA encoding 16S rRNA or 23S rRNA and a portion of said DNA flanking said DNA encoding 16S rRNA or 23S rRNA;

separating said digestion products for each of said isolates;

detecting said digestion products for each of said isolates; and grouping said isolates based on the number of digestion products having identical size to define one or more subsets of isolates.

10. The method of claim 7, wherein said conserved amino acid sequence is present in more than 80% of said isolate subsets.

11. The method of claim 7, wherein said conserved amino acid sequence appears in said candidate vaccine target antigen in disease causing said isolates but does not appear in said candidate vaccine target antigen in harmless said isolates.

12. The method of claim 1 or claim 2, further comprising the step of testing a candidate antibody to said vaccine target antigen from said representative isolate for reactivity.

13. The method of claim 1 or claim 2, further comprising the steps of identifying in said candidate vaccine target antigen an amino acid sequence that is conserved among said isolate subsets and synthesizing said amino acid sequence to produce a test peptide vaccine.

14. A method of immunizing a mammal, said method comprising the steps of:

a) providing a mammal in need of immunization; and b) immunizing said mammal with a peptide vaccine, wherein said vaccine has been developed by the method of claim 13.

* * * * *